(12) United States Patent
Robertson et al.

(10) Patent No.: US 11,000,297 B2
(45) Date of Patent: May 11, 2021

(54) ORTHOPAEDIC SURGICAL INSTRUMENTATION FOR PERFORMING A PATELLOFEMORAL ARTHROPLASTY PROCEDURE

(71) Applicant: DEPUY SYNTHES PRODUCTS, INC., Raynham, MA (US)

(72) Inventors: Lisa Robertson, Warsaw, IN (US); Daniel Auger, Fort Wayne, IN (US); Matthew Wallace, Huntertown, IN (US); Jack Farr, II, Bargersville, IN (US); Scott Brown, Warsaw, IN (US); Dimitri Sokolov, San Jose, CA (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 273 days.

(21) Appl. No.: 15/892,439

(22) Filed: Feb. 9, 2018

(65) Prior Publication Data

US 2018/0161049 A1    Jun. 14, 2018

Related U.S. Application Data

(62) Division of application No. 14/474,237, filed on Sep. 1, 2014, now Pat. No. 9,895,156, which is a division
(Continued)

(51) Int. Cl.
*A61B 17/17* (2006.01)
*A61B 17/16* (2006.01)
(Continued)

(52) U.S. Cl.
CPC ........ *A61B 17/1767* (2013.01); *A61B 17/155* (2013.01); *A61B 17/1615* (2013.01);
(Continued)

(58) Field of Classification Search
CPC .................. A61B 17/1764; A61B 17/1767
See application file for complete search history.

(56) References Cited

U.S. PATENT DOCUMENTS

| 2,349,394 A | 5/1944 | Widdis |
| 4,721,104 A | 1/1988 | Kaufman et al. |
| (Continued) | | |

FOREIGN PATENT DOCUMENTS

| EP | 685210 | 12/1995 |
| EP | 1374782 | 1/2004 |
| (Continued) | | |

OTHER PUBLICATIONS

European Search Report for European Patent Application No. 11185257.0-2310, dated Mar. 29, 2012, 6 pages.
(Continued)

*Primary Examiner* — Nicholas W Woodall
(74) *Attorney, Agent, or Firm* — Barnes & Thornburg LLP

(57) ABSTRACT

A method and instrumentation for performing a patellofemoral arthroplasty orthopaedic procedure includes coupling an anterior cutting block to a femur of a patient such that the cutting block references local anatomy of the femur. The anterior cutting block is used to perform a number of bone cuts to establish a trochlear cavity in the femur. The trochlear cavity is formed such that a trochlear prosthesis may be inset into the cavity and substantially flush with the surrounding cartilage. A finishing burring guide and burr bit may be used to detail the shape and/or size of the trochlear cavity. Additionally, a trochlear drill guide may be used to facilitate establishing peg holes in the patient's femur to receive corresponding pegs of the trochlear prosthesis.

5 Claims, 26 Drawing Sheets

Related U.S. Application Data of application No. 12/512,539, filed on Jul. 30, 2009, now Pat. No. 8,828,016.

(60) Provisional application No. 61/085,805, filed on Aug. 1, 2008.

(51) Int. Cl.
*A61B 17/15* (2006.01)
*A61F 2/38* (2006.01)
*A61B 17/14* (2006.01)

(52) U.S. Cl.
CPC ...... *A61B 17/1675* (2013.01); *A61B 17/1764* (2013.01); *A61B 17/142* (2016.11); *A61B 17/144* (2016.11); *A61F 2/3877* (2013.01)

(56) References Cited

U.S. PATENT DOCUMENTS

| | | | |
|---|---|---|---|
| 5,098,436 A * | 3/1992 | Ferrante | A61B 17/1659 |
| | | | 606/53 |
| 5,141,513 A | 8/1992 | Fortune | |
| 5,176,684 A | 1/1993 | Ferrante et al. | |
| 5,234,433 A | 8/1993 | Bert et al. | |
| 5,312,411 A * | 5/1994 | Steele | A61B 17/1675 |
| | | | 606/79 |
| 5,324,295 A * | 6/1994 | Shapiro | A61B 17/1714 |
| | | | 606/86 R |
| 5,344,423 A * | 9/1994 | Dietz | A61B 17/1764 |
| | | | 606/86 R |
| 5,474,559 A | 12/1995 | Bertin et al. | |
| 5,554,158 A | 9/1996 | Vinciguerra et al. | |
| 5,593,411 A * | 1/1997 | Stalcup | A61B 17/1764 |
| | | | 606/87 |
| 5,601,563 A | 2/1997 | Burke et al. | |
| 5,624,445 A | 4/1997 | Burke | |
| 5,662,656 A | 9/1997 | White | |
| 5,683,397 A | 11/1997 | Vendrely et al. | |
| 5,688,279 A | 11/1997 | McNulty et al. | |
| 5,702,459 A | 12/1997 | Hummer et al. | |
| 5,709,689 A | 1/1998 | Ferrante et al. | |
| 5,921,988 A * | 7/1999 | Legrand | A61B 17/1728 |
| | | | 606/87 |
| 6,554,838 B2 | 4/2003 | McGovern et al. | |
| 7,488,326 B2 | 2/2009 | Elliott | |
| 7,678,115 B2 * | 3/2010 | D'Alessio, II | A61B 17/155 |
| | | | 606/86 R |
| 7,806,898 B2 * | 10/2010 | Justin | A61B 17/1675 |
| | | | 606/85 |
| 7,963,968 B2 | 6/2011 | Dees | |
| 8,105,330 B2 | 1/2012 | Fitz et al. | |
| 8,282,646 B2 | 10/2012 | Schoenefeld et al. | |
| 8,298,237 B2 | 10/2012 | Schoenefeld et al. | |
| 8,323,288 B2 | 12/2012 | Zajac | |
| 8,828,016 B2 | 9/2014 | Major et al. | |
| 8,852,195 B2 * | 10/2014 | Justin | A61B 17/1675 |
| | | | 606/87 |
| 8,920,427 B2 | 12/2014 | Major et al. | |
| 9,468,448 B2 | 10/2016 | Sikora | |
| 9,895,156 B2 | 2/2018 | Robertson et al. | |
| 2001/0001121 A1 | 5/2001 | Lombardo et al. | |
| 2002/0183760 A1 * | 12/2002 | McGovern | A61B 17/1764 |
| | | | 606/88 |
| 2004/0153066 A1 | 8/2004 | Coon et al. | |
| 2004/0153162 A1 * | 8/2004 | Sanford | A61F 2/4684 |
| | | | 623/20.3 |
| 2005/0187560 A1 | 8/2005 | Dietzel et al. | |
| 2006/0173463 A1 | 8/2006 | Dees | |
| 2006/0276796 A1 * | 12/2006 | Creger | A61B 17/1767 |
| | | | 606/79 |
| 2007/0293870 A1 * | 12/2007 | Colquhoun | A61B 17/1764 |
| | | | 606/96 |
| 2008/0114370 A1 | 5/2008 | Schoenefeld et al. | |
| 2008/0161815 A1 | 7/2008 | Schoenefeld et al. | |
| 2008/0281329 A1 | 11/2008 | Fitz et al. | |
| 2009/0099567 A1 | 4/2009 | Zajac | |

FOREIGN PATENT DOCUMENTS

| | | |
|---|---|---|
| GB | 2398011 | 8/2004 |
| WO | 2005069809 | 8/2005 |
| WO | 2006127486 A2 | 11/2006 |

OTHER PUBLICATIONS

"Nexgen Solution: Innovating Instrumentation With Multiple Customization Options Designed to Enhance Precision of Implant Fit and Alignment", 7 pages.

International Search Report for International Application No. PCT/US2009/052251, dated Jan. 19, 2010, 20 pages.

"AVON Patello-femoral Arthroplasty—Surgical Technique," Stryker Howmedica Osteonics—www.avonpatella.com, Aug. 2003, 12 pages.

"Vanguard Completed Knee System—Vanguard Knee Surgical Technique," Biomet UK Ltd, Mar. 2006, 16 pages, FLK 155, Bridgend, South Wales, United Kingdom.

"Zimmer MIS Natural-Knee II Unicompartmental Knee System—Bone Conserving," Zimmer—www.zimmer.com, 2004-2005, 6 pages, 00-1001-01-011—Rev 4.

"Smith & Nephew Journey Bi-Cruciate Stabilized Knee System—Surgical Technique," Smith & Nephew, Inc.—www.smith-nephew.com, Mar. 2006, 54 pages, 40490101.

"LCS Complete Mobile-Bearing Knee System—Surgical Technique—Milestone Instruments with M.B.T. Tray Preparation," DePuy—a Johnson & Johnson Company, 42 pages.

* cited by examiner

ORTHOPAEDIC SURGICAL INSTRUMENTATION FOR PERFORMING A PATELLOFEMORAL ARTHROPLASTY PROCEDURE

CROSS-REFERENCE TO RELATED U.S. PATENT APPLICATIONS

This application claims priority under 35 U.S.C. § 121 to U.S. Utility patent application Ser. No. 14/474,237, now U.S. Pat. No. 9,895,156, which claimed priority under 35 U.S.C. § 121 to U.S. Utility patent application Ser. No. 12/512,539, now U.S. Pat. No. 8,828,016, which claimed priority under 35 U.S.C. § 119(e) to U.S. Provisional Patent Application Ser. No. 61/085,805 entitled "Method and Instrumentation for Performing a Patellofemoral Arthroplasty Orthopaedic Procedure," by Lisa Major et al., which was filed on Aug. 1, 2008, the entirety of each which is hereby incorporated by reference.

Cross-reference is also made to U.S. Utility patent application Ser. No. 12/512,543, now U.S. Pat. No. 8,920,427, entitled "Orthopaedic Surgical Method for Performing a Patellofemoral Arthroplasty Procedure," by Lisa Major et al., the entirety of which is hereby incorporated by reference.

TECHNICAL FIELD

The present disclosure relates generally to methods and instrumentation for performing an orthopaedic surgical procedure, and particularly to methods and associated instrumentation for performing a patellofemoral arthroplasty orthopaedic surgical procedure.

BACKGROUND

Joint arthroplasty is a surgical procedure by which a diseased and/or damaged natural joint is replaced by a prosthetic joint. Patellofemoral arthroplasty is a type of joint arthroplasty wherein the anterior compartment of a patient's knee, or portion thereof, is replaced with one or more prosthetic components. Additionally, in some cases, the patient's patella may be replaced by an orthopaedic prosthesis.

Typical patellofemoral arthroplasty procedures may include replacing a patient's femoral trochlea, and in some cases, one or both femoral condyles with prosthetic components. Typical orthopaedic surgical procedures require the entire anterior femur to be resectioned to allow overlay of the prosthetic joint components. However, the prosthetic joint components may not replace the entire volume of resectioned bone. Additionally, many patellofemoral arthroplasty procedures and instrumentation reference off of the intramedullary canal of the patient's femur, which resultantly compromises the intrameduallary canal.

SUMMARY

According to one aspect, an orthopaedic surgical instrument may include a femoral cutting block. The femoral cutting block may include a body, a first vertical cutting guide, a second vertical cutting guide and a horizontal cutting guide. The body may have a bone-facing surface having a contour corresponding to at least a portion of an upper surface of an associated trochlear prosthesis. The femoral cutting block may also include a distal boss extending outwardly from the bone-facing surface. The distal boss may include a first passageway extending therethrough.

In some embodiments, the first and second vertical cutting guides may be embodied as open cutting guides. Additionally, the horizontal cutting guide may be embodied as a closed cutting guide. The first vertical cutting guide may define a first cutting plane and the second vertical cutting guide may define a second cutting plane. In some embodiments, the second cutting plane may be non-parallel to the first cutting plane. Additionally, in some embodiments, the first vertical cutting guide may be embodied as a medial cutting guide, the second vertical cutting guide may be embodied as a lateral cutting guide, and the horizontal cutting guide may be embodied as an anterior cutting guide. The first vertical cutting guide may be defined by a first sidewall extending upwardly from the body a first distance and the second vertical cutting guide may be defined by a second sidewall extending upwardly from the body a second distance. In some embodiments, the second distance being greater than the first distance.

In some embodiments, the femoral cutting block may also include an arm removably coupled to the body and extending therefrom. In such embodiments, the femoral cutting block may include a boss extending upwardly from an upper surface of the body. The arm may include an aperture sized to receive the boss to couple the arm to the body. Additionally, the arm may be pivotable about the boss. In some embodiments, the boss may include an upper surface and an alignment line defined on the upper surface. In such embodiments, the alignment line may be substantially perpendicular to the bone-facing surface of the body.

In some embodiments, the body may include an upper body section and a lower body section extending downwardly from the upper body section. The lower body section may include a second passageway oblique to the first passageway. Additionally, in some embodiments, the femoral cutting block may include a tab extending downwardly from the lower body section. The tab may be positioned and sized to contact the distal cartilage of a patient's femur when the femoral cutting block is coupled thereto. For example, in some embodiments, the tab may extend downwardly from the lower body section a distance of about two millimeters. Additionally, the femoral cutting block may include a mount coupled to an upper surface of the body, the mount being configured to couple with a tool to position the orthopaedic surgical instrument without touching the femoral cutting block.

According to another aspect, an orthopaedic burring guide may include a frame having a curved bone-facing side. The frame may define a first opening and a second opening separate from the first opening. The burring guide may also include a distal boss extending from the bone-facing side of the frame. The distal boss may include a passageway defined therein. The orthopaedic burring guide may further include a base extending downwardly from the frame. The base may be sized to be received in a surgically-prepared trochlear cavity of a patient's anterior femur. The base may include a first and second mounting hole defined therethrough. In some embodiments, the orthopaedic burring guide may also include a tab extending downwardly from the distal boss. In such embodiments, the tab may have a length less than the distal boss. Additionally, in some embodiments, the base may have a thickness substantially equal to the depth of the anterior trochlear cavity.

According to another aspect, a trochlear drill guide may include a body having a first passageway and a second passageway defined therethrough, a first drill guide bushing positioned in the first passageway, and a second drill guide bushing positioned in the second passageway. The first drill guide bushing may be movable within the first passageway. The first drill guide bushing may also include a first inner passageway defined therethrough. Similarly, the second drill guide bushing may be movable within the second passageway and may include a second inner passageway defined therethrough.

In some embodiments, the first and second drill guide bushings may be separately movable. Additionally, the first and second drill guide bushings may be movable along a longitudinal axis defined by the respective first and second passageways. Further, in some embodiments, the first drill guide bushing may include a first end, a first collar coupled to the first end, a second end opposite the first end, and a second collar coupled to the second end. In such embodiments, the first drill guide bushing may be movable within the first passageway between a first position in which the first collar extends out of the first passageway and a second position wherein the second collar extends out of the first passageway. Similarly, the second drill guide bushing may include a third end, a third collar coupled to the third end, a fourth end opposite the third end, and a fourth collar coupled to the fourth end. The second drill guide bushing may be movable within the second passageway between a third position in which the third collar extends out of the second passageway and a fourth position wherein the fourth collar extends out of the second passageway.

In some embodiments, the trochlear drill guide may also include a mount coupled to the body and extending therefrom. The mount may include a first mounting base located at a first end and a second mounting base located at a second end opposite the first end. The mount may define a keyed structure to be received in a corresponding keyed recess. For example, in some embodiments, the mount may include a first keyed protrusion extending from a first side of the first mounting base and a second keyed protrusion extending from a second side of the second mounting base.

BRIEF DESCRIPTION OF THE DRAWINGS

The detailed description particularly refers to the following figures, in which.

DETAILED DESCRIPTION OF THE DRAWINGS

Figure 1A:
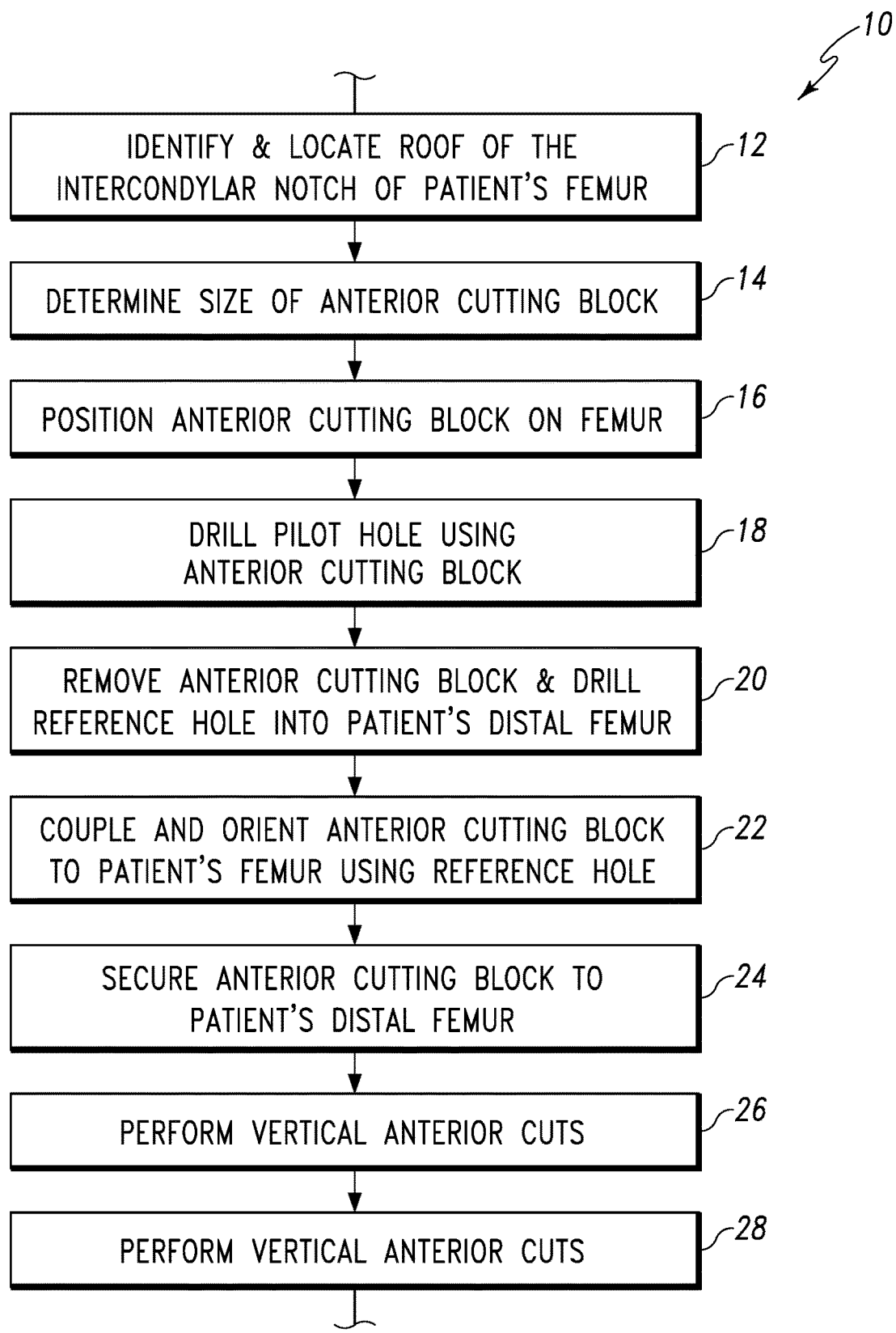
FIGS. 1A and 1B are a flowchart of a method for performing an orthopaedic surgical procedure.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout this disclosure in reference to both the orthopaedic implants described herein and a patient's natural anatomy. Such terms have well-understood meanings in both the study of anatomy and the field of orthopaedics. Use of such anatomical reference terms in the specification and claims is intended to be consistent with their well-understood meanings unless noted otherwise.

Figure 1B:
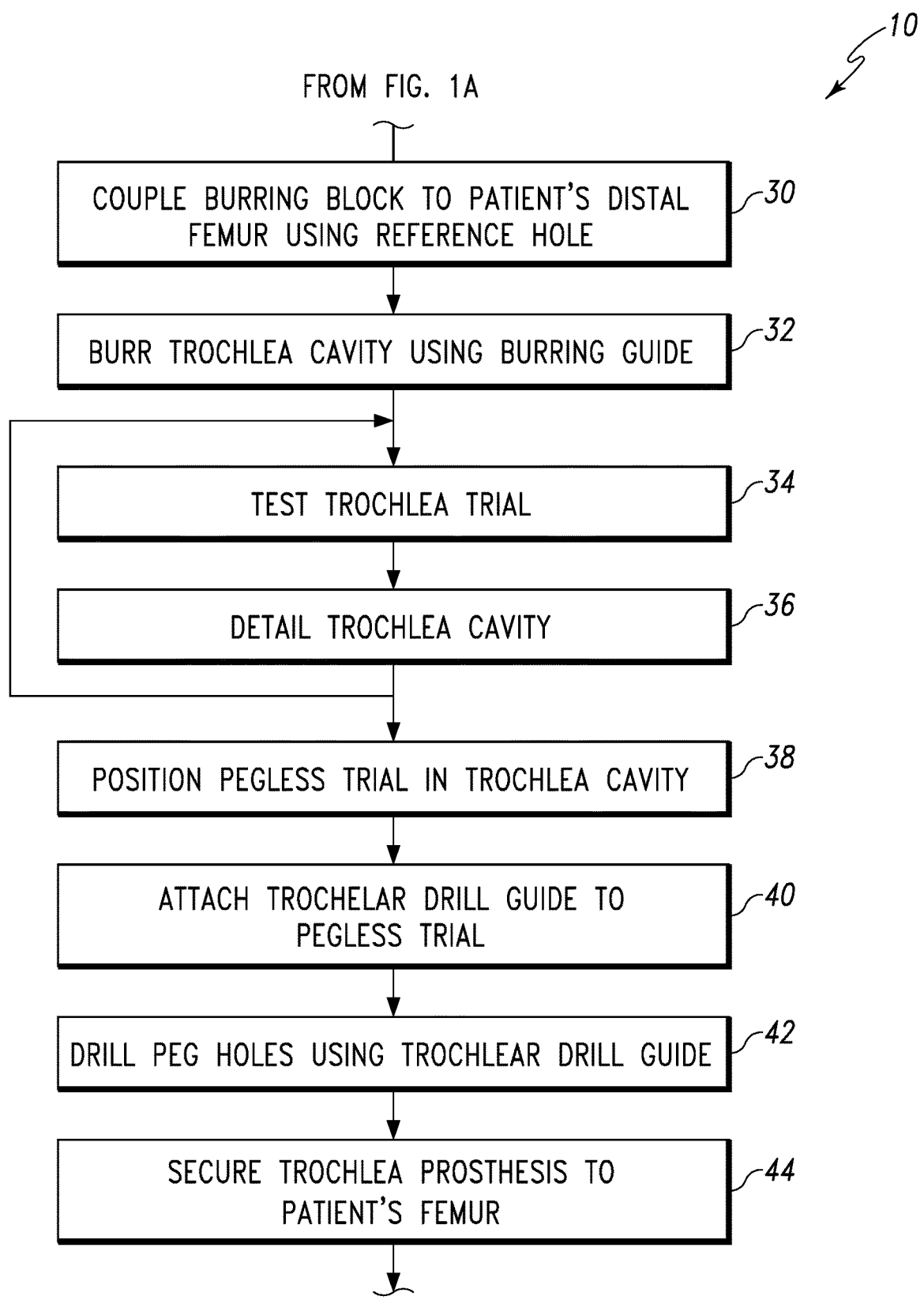
Figure 2:
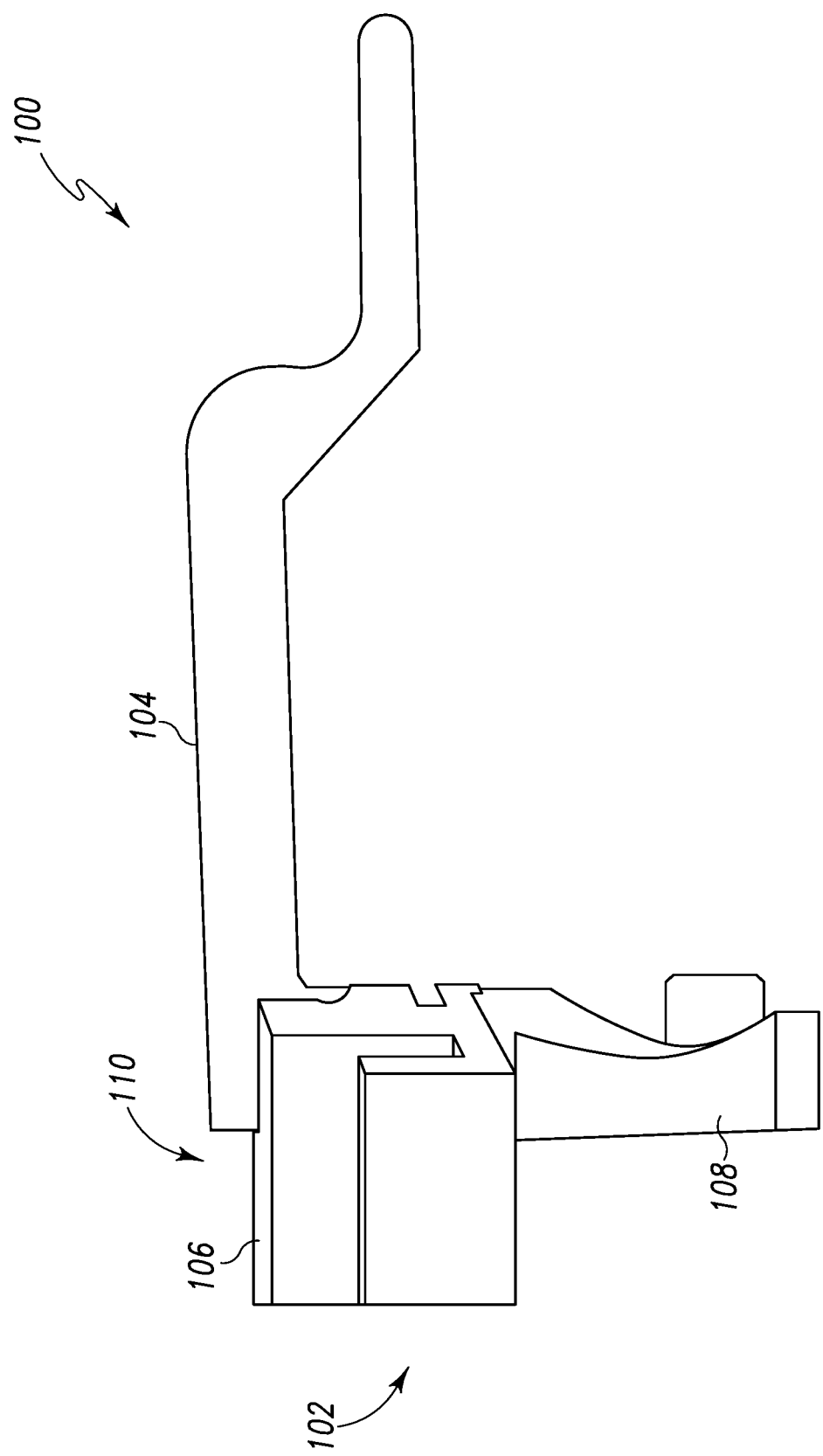
FIG. 2 is a side elevational view of an anterior femoral cutting block for use with the method of FIG. 1.
Figure 3:
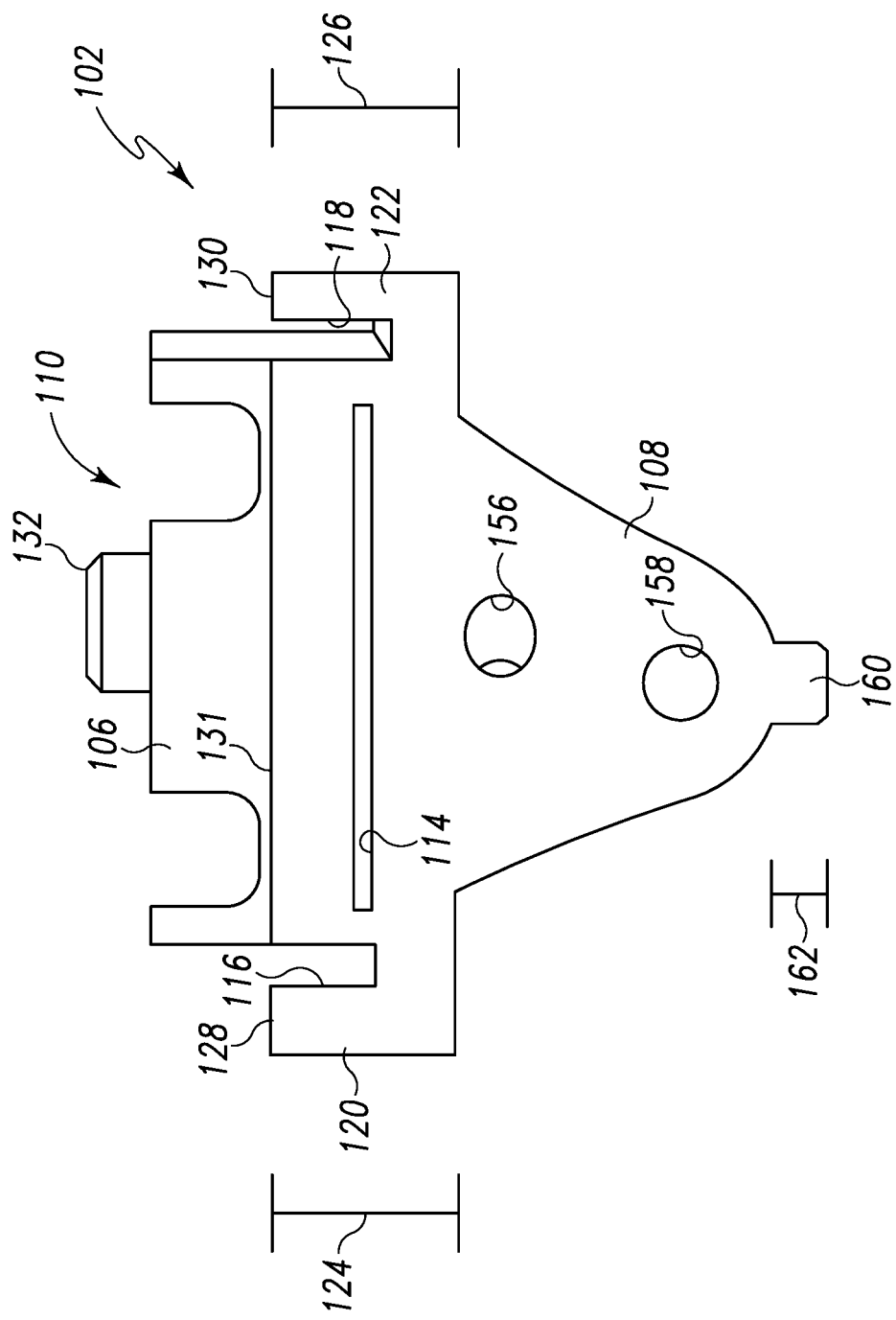
FIG. 3 is a front elevational view of the anterior femoral cutting block of FIG. 2.
Figure 4:
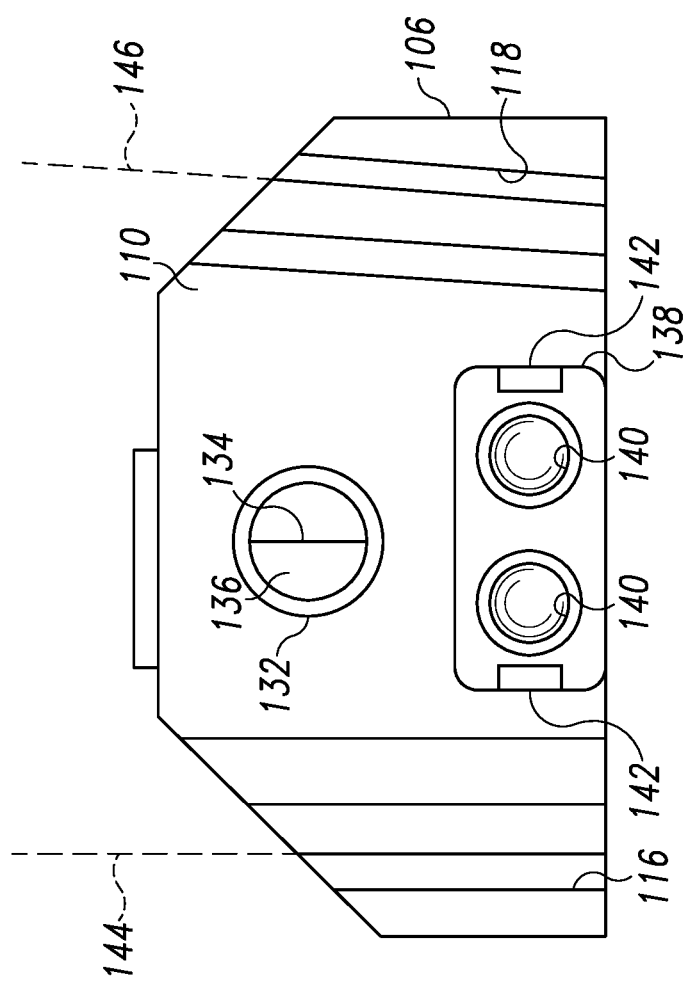
FIG. 4 is a top plan view of the anterior femoral cutting block of FIG. 2.

A method 10 for performing a patellofemoral arthroplasty orthopaedic procedure to replace a portion of a patient's femoral trochlea with a trochlear orthopaedic prosthesis is illustrated in FIGS. 1a and 1b. The method 10 begins with a step 12 in which a reference point of the patient's relevant femur is located. This reference point is used throughout the method 10 to position various surgical instrumentation as discussed in more detail below. In the embodiment of FIG. 1, the local reference point is defined as the roof of the intercondylar notch of the patient's relevant femur. Once identified, this reference point is used to position the surgical instruments by referencing each instrument to the roof of the patient's intercondylar notch.

After the reference point has been determined in step 12, an anterior femoral cutting block 100 is sized and coupled to the patient's relevant femur in step 14. The anterior femoral cutting block 100 is used to perform a number of bone cuts on the patient's femur as discussed in more detail below. One embodiment of an anterior femoral cutting block 100 used with the method 10 is illustrated in FIGS. 2-14. The cutting block 100 includes a cutting block body 102 and a sizing arm 104 coupled to the cutting block body 102. The cutting block body 102 includes an upper body 106 and a lower body 108 extending downwardly from the upper body 106. The sizing arm 104 is coupled to a top side 110 of the upper body 106. In the illustrative embodiment, the upper body 106 has a substantially rectangular shape and the lower body 108 has a substantially triangular shape. However, in other embodiments, the upper and lower bodies 106, 108 of the cutting block 100 may have other shapes.

The upper body 106 of the cutting block body 102 includes a horizontal cutting guide 114 and two vertical cutting guides 116, 118. In the illustrative embodiment, the horizontal cutting guide 114 is embodied as a captured cutting guide and the vertical cutting guides 116, 118 are embodied as non-captured or opened cutting guides. However, in other embodiments, other types of cutting guides may be used.

Figure 6:
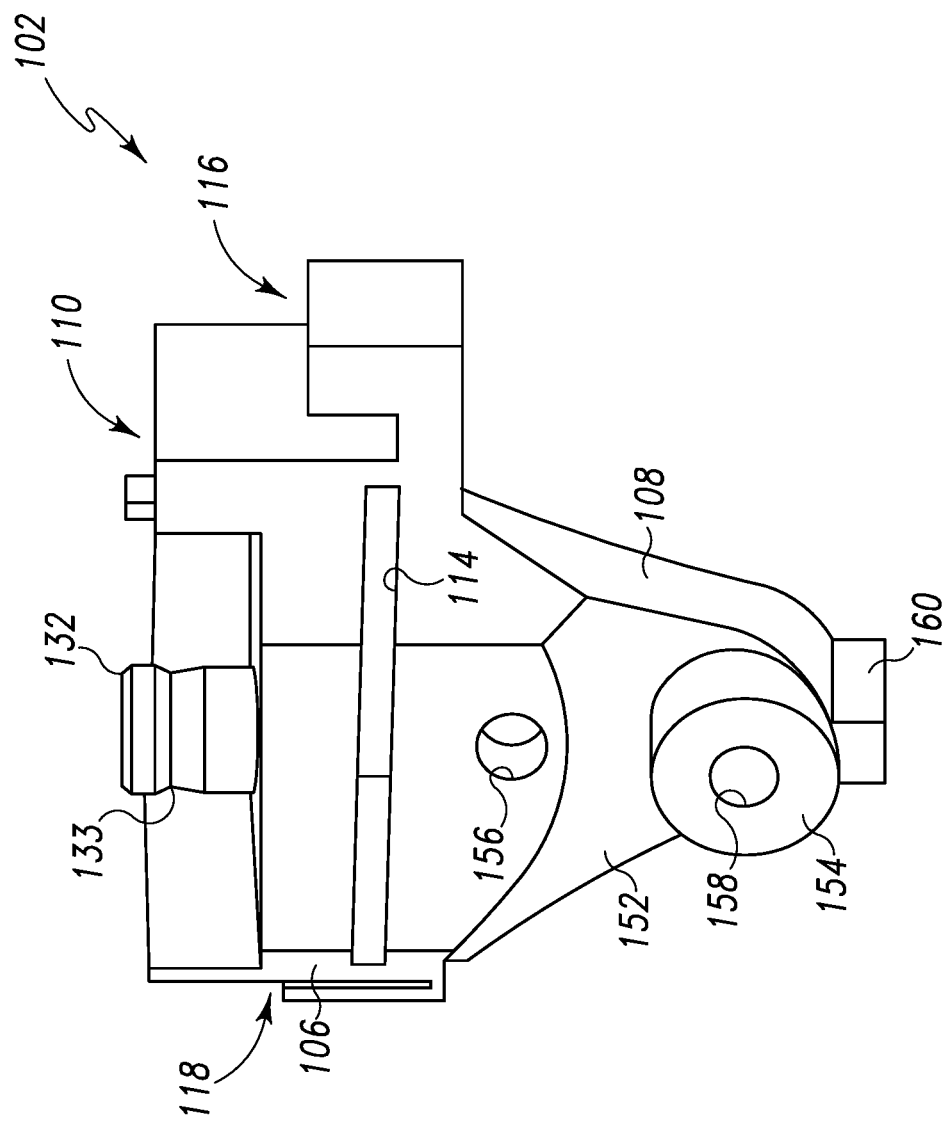
FIG. 6 is a rear perspective view of the anterior femoral cutting block of FIG. 2.

The vertical cutting guide 116 is defined, in part, by a side wall 120 that extends upwardly from the upper body 106. Similarly, the vertical cutting guide 118 is defined, in part, by a side wall 122 that extends upwardly from the upper body 106. In the illustrative embodiment, the side walls 120, 122 have different heights. That is, the wall 120 extends upwardly from the upper body 106 a distance 124 and the wall 122 extends upwardly from the upper body 106 a distance 126 that is different from the distance 124. However, in other embodiments, the walls 120, 122 may extend upwardly from the upper body 106 the same distance (i.e., the distances 124 and 126 may be substantially equal). Each of the walls 122, 124 includes a top surface 128, 130, respectively, which are used to axially align the anterior femoral cutting block 100 relative the patient's femur as discussed in more detail below. In the illustrative embodiments, the vertical cutting guides 116, 118 are defined such that the cutting planes defined thereby are non-parallel. That is, as illustrated in FIG. 6, a cutting plane 144 defined by the vertical cutting guide 116 is non-parallel to a cutting plane 146 defined by the cutting guide 118. However, in other embodiments, the vertical cutting guides 116, 118 may define parallel cutting planes (i.e., the cutting planes 144, 146 may be substantially parallel). In some embodiments, the upper body 106 may include a line or indicia 131 extending between and aligned with the top surfaces 128, 130 of the walls 120, 122, which may be used to orient the anterior cutting block 102 as discussed in more detail below.

As discussed above, the upper body 106 of the cutting block body 102 includes a top side 110 to which the sizing arm 104 is coupled. A peg or boss 132 extends upwardly from the top side 110. The peg 132 is used to couple the sizing arm 104 to the block body 102. In one particular embodiment, the peg 132 includes a circumferential groove 133 (see FIG. 6) to mate with a BAL SEAL® spring assembled into the sizing arm 104. When coupled, the sizing arm 104 is free to rotate about the peg 132. In some embodiments, the peg 132 may include an alignment line or indicia 134 (see FIG. 4) defined on a top surface 136 of the boss 132. The alignment line 134 is perpendicular to a bone-facing side of the cutting block body 102. The alignment line 134 may be used to align the sizing arm 104 in a position that is substantially perpendicular to the cutting block body 102. To do so, the sizing arm 104 may be rotated about the boss 132. In some embodiments, the sizing arm 104 may include a corresponding alignment line 135 (see FIG. 13), which may be used to align the sizing arm 104 relative to the cutting block body 102 by aligning the lines 134, 135.

The top side 110 of the upper body 106 may also include a base 138 for coupling a positioning clamp 310 (see FIG. 8) to the cutting block body 102. The illustrative base 138 includes a pair of apertures 140 and vertically extending tabs 142 positioned toward the sides of the apertures 140. The apertures 140 and tabs 142 provide a structure to which the positioning clamp 310 may be coupled to allow the clamp 310 to properly position the cutting block body 102.

Figure 5:
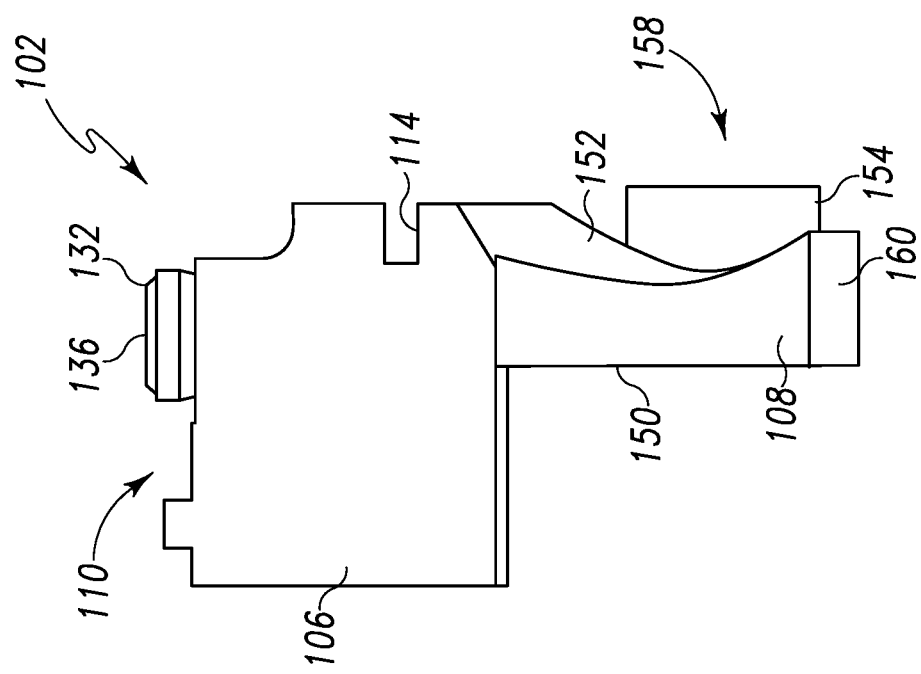
FIG. 5 is a side elevational view of the anterior femoral cutting block of FIG. 2.

As shown in FIG. 5, the lower body 108 of the cutting block body 102 includes an outer side 150 and a bone-confronting side 152. The outer side 150 of the lower body 108 may be substantially planar. However, the bone-confronting side 152 of the lower body 108 is contoured or otherwise curved. In the illustrative embodiment, the curvature of the bone-confronting side 152 matches the curvature of a trochlear orthopaedic prosthesis or implant 300 (see FIG. 7). As such, the cutting block body 102 is configured for use with a particular size and side (right knee or left knee implant) of a trochlear prosthesis 300. When the anterior femoral cutting block 100 is coupled to the femur of a patient, the bone-confronting side 152 abuts or confronts the patient's femoral cartilage. As such, the *Varus*/Valgus alignment of the anterior cutting block 100 can be evaluated by assessing the quality of fit or conformity of the medial and lateral sides of the bone-confronting side 152.

The lower body 108 of the cutting block body 102 also includes a distal boss 154, which extends outwardly from the bone-confronting side 152. As discussed below, the boss 154 is configured to be inserted into a reference hole or cavity previously formed in the patient's femur to secure and align the anterior femoral cutting block 100 to the patient's femur. The lower body 108 also includes a pair of pin guide holes 156, 158 defined therethrough. The pin guide holes 156, 158 are used to secure the anterior cutting block 102 to the patient's femur using a pair of bone pins or similar fixation devices. The pin guide hole 158 extends through the distal boss 154. The pin guide hole 156 is located superiorly and angled relative to the pin guide hole 158 to prevent or otherwise limit the cutting block body 102 from backing off the bone pins during use (e.g., from vibrations generated by a bone saw).

The cutting block body 102 also includes a distal tab 160 that extends downwardly from the lower body 108. Illustratively, the tab 160 extends from the lower body 108 a distance 162 (see FIG. 3) such that the tab 160 references or otherwise contacts the distal articular cartilage of the patient's femur when coupled thereto. In this way, the anterior cutting block 102 references the distal articular cartilage. In the illustrative embodiment, the distal tab 160 extends from the lower body 108 a distance 162 equal to about 2 millimeters. However, in other embodiments, the tab 160 may extend from the lower body 108 a different distance.

It should be appreciated that the anterior cutting block 102 is usable to perform a number of different functions. For example, the size and alignment of the trochlear prosthesis 300 is determined using the cutting block 102. Additionally, the vertical cutting guides 116, 118 facilitate vertical resections, which allow a flat, anterior cut using the horizontal cutting guide 114 to be utilized in the surgical technique method. This horizontal and vertical resectioning cuts form a trochlear cavity that allows at least a portion of the trochlear implant to be inlaid. Additionally, the anterior femoral cutting block 100 includes the boss 132, which locks the sizing arm 104 to the block 102 using BAL SEAL® springs. The anterior femoral cutting block 100 also includes the distal boss 154, which references a previously prepared reference hole defined in the patient's distal femur. Additionally, the bone-confronting side 152 of the cutting block body 102 is contoured to match the articulating geometry of the respective trochlear implant.

Figure 7:
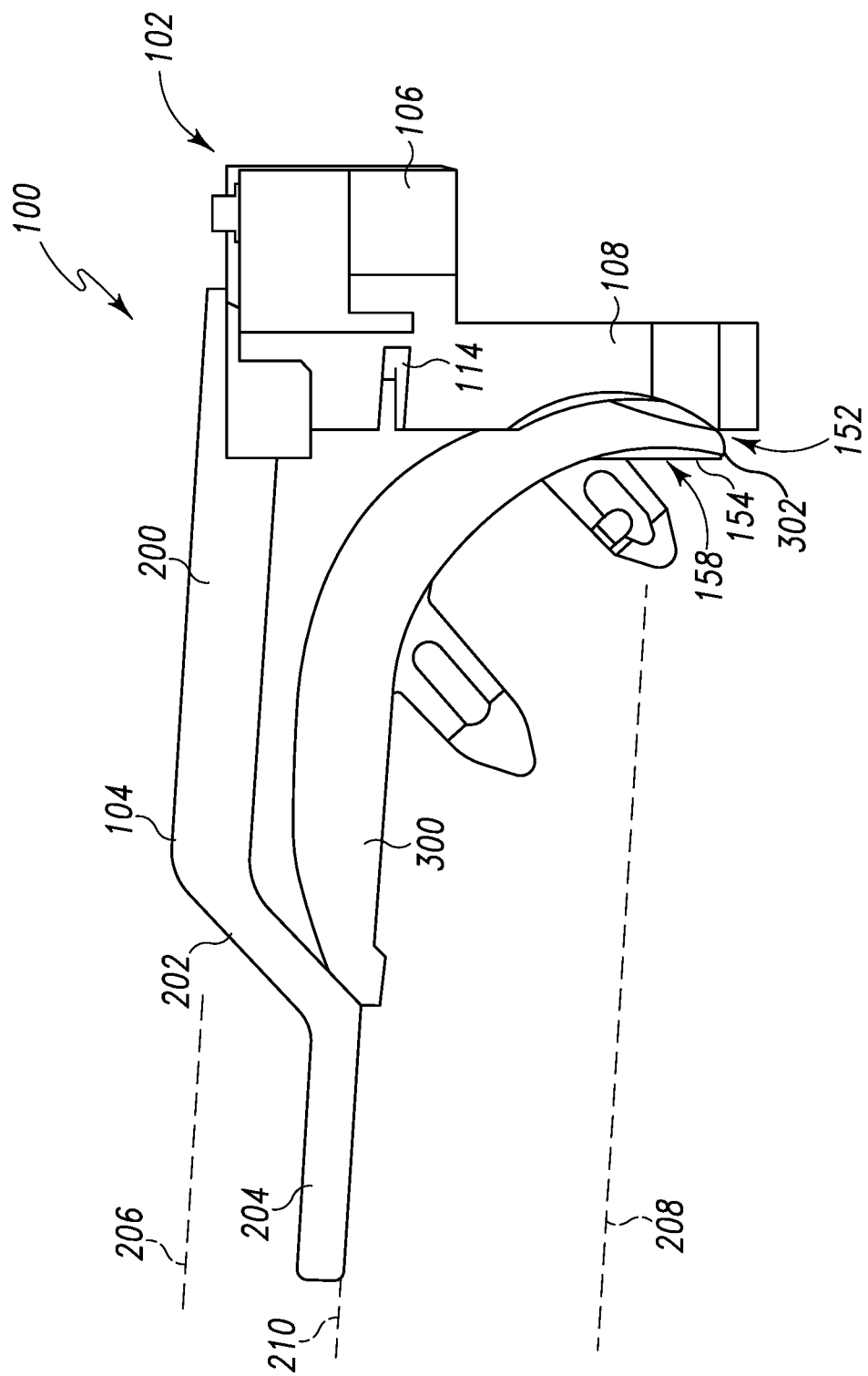
FIG. 7 is another side elevational view of the anterior femoral cutting block of FIG. 2.

As discussed above, the sizing arm 104 is coupled to the peg 132 extending upwardly from the top side 110 of the cutting block body 102. As shown in FIG. 7, the sizing arm 104 includes an elongated shaft 200, a angled arm 202, and a proximal end shaft 204. The proximal end shaft 204 is offset from an axis 206 defined by the elongated shaft 200 via the angled arm 202. In one embodiment, the proximal end shaft 204 is substantially parallel to the axis 206, but may be angled with respect thereto in other embodiments. In use, as discussed below, the sizing arm 104 is used to reference the anterior cortex of the patient's femur. The proximal end shaft 204 is angled about three degrees relative to an axis 208 defined by the guide pin hole 158 of the distal boss 154 of the cutting block body 102. The bottom side of the proximal end shaft 204 is in alignment with a horizontal cutting plane 210 defined by the horizontal cutting guide 114. The sizing arm 104 may be used to predict or otherwise identify the orientation and location of the anterior resection.

As discussed above, the anterior femoral cutting block 100 is used to select the appropriate size of the trochlear orthopaedic prosthesis 300. In particular, the trochlear prosthesis 300 is selected such that the prosthesis 300 is positionable within the cutting block 100 such that the distal end of the prosthesis 300 is received in the contoured bone-confronting surface 152 of the cutting block body 102 and the superior end of the prosthesis 300 contacts the sizing arm 104. When so positioned, the bottom side of the superior end of the prosthesis 300 is substantially planar with the cutting plane 210 defined between the horizontal cutting guide 114 and the proximal end shaft 204 of the sizing arm 104.

Figure 8:
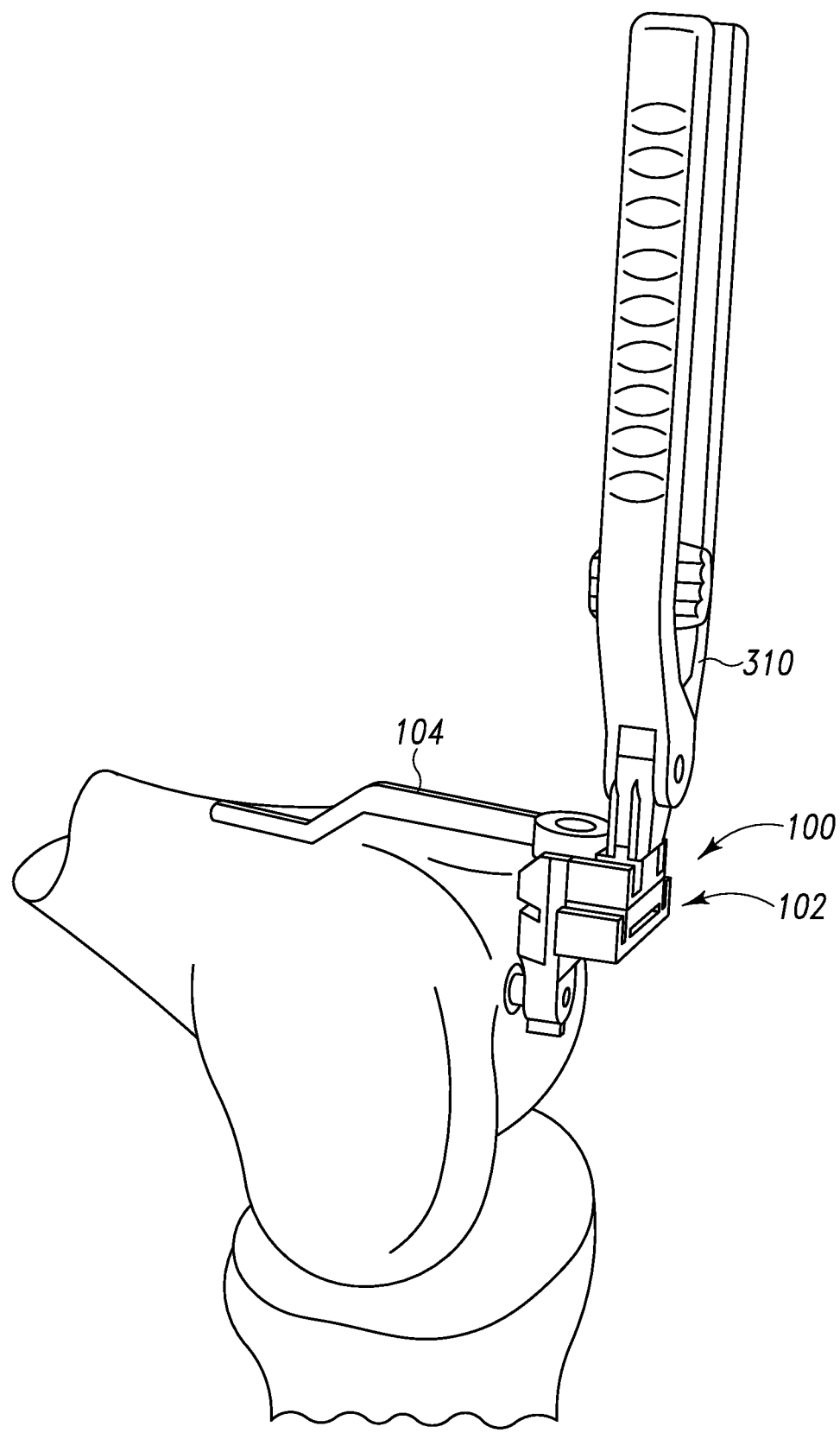
FIG. 8 is a perspective view of the anterior femoral cutting block of FIG. 2 positioned on the distal end of a patient's femur.

Referring back to FIG. 1, after the anterior femoral cutting block 100 has been sized according to the particular trochlear orthopaedic prosthesis 300 to be implanted and the patient's anatomy, the cutting block 100 is positioned on the distal end of the patient's femur. To do so, as illustrated in FIG. 8, a positioning clamp 310 is coupled to the cutting block body 102. The clamp 310 is secured to the body 102 via the base 138. As discussed above, the apertures 140 and tabs 142 of the base 138 provide a structure to which the positioning clamp 310 is coupled. The clamp 310 may be held by the orthopaedic surgeon or other healthcare provider while positioning the cutting block 100 on the patient's femur. The cutting block 100 is positioned on the distal end of the patient's femur such that the sizing arm 104 references the anterior cortex of the patient's femur and the distal tab 160 references the distal articular cartilage (i.e., the reference point determined in block 12) of the patient's femur. When so positioned, the bottom side of the distal boss 160 is about two to three millimeters from the roof of the intercondylar notch. Such positioning of the cutting block 100 facilitates the forming of a similarly positioned trochlear cavity and, thereby, positions the trochlear orthopaedic prosthesis 300 about two to three millimeters from the roof of the intercondylar notch.

Figure 9:
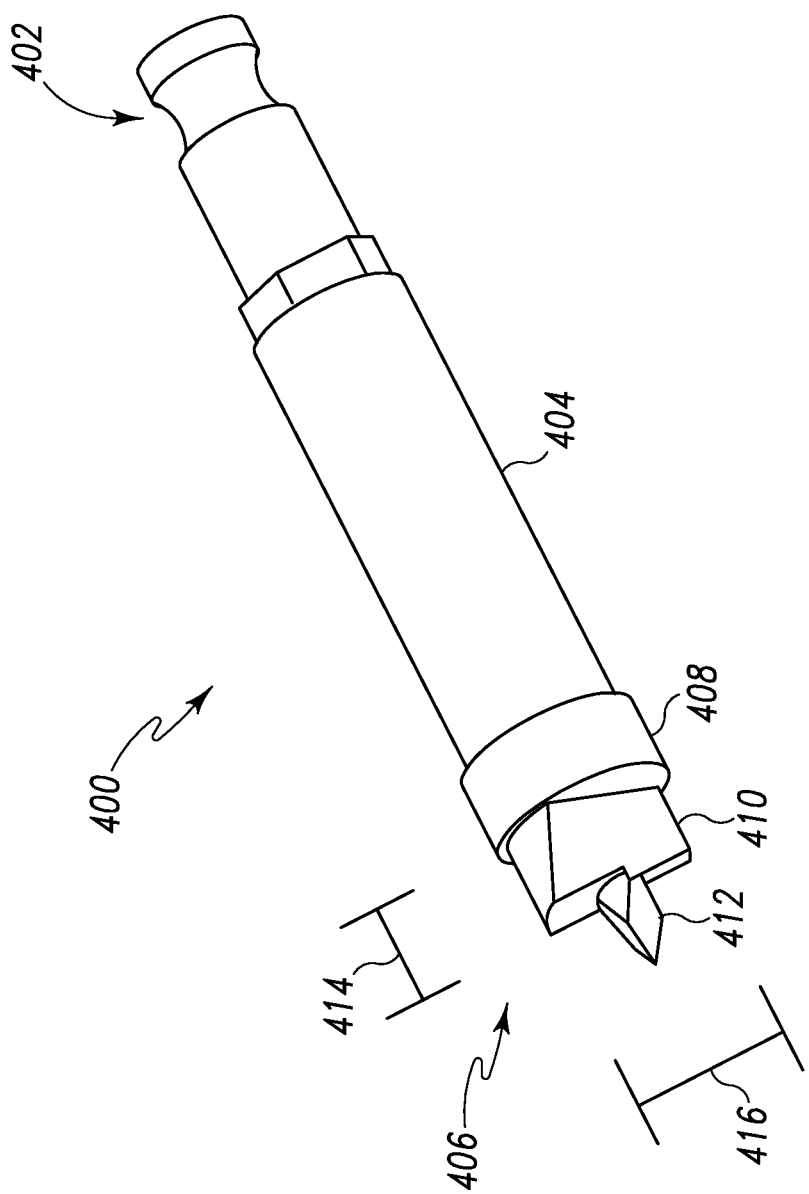
FIG. 9 is a perspective view of a drill bit used in the method of FIG. 1.

Referring back to FIG. 1, after the anterior femoral cutting block 100 has been properly positioned on the distal end of the patient's femur, a pilot or starter hole is drilled into the distal end of the patient's femur in step 18. To do so, the orthopaedic surgeon uses the guide pin hole 158 of the block 100 as a drill guide to establish the pilot hole. After the pilot hole has been formed in the patient's distal femur, the anterior femoral cutting block 100 is removed from the patient's femur and a reference hole is formed in the distal end of the patient's femur in block 20. To do so, the orthopaedic surgeon uses a pilot drill bit 400, which references the pilot hole formed in step 18. As illustrated in FIG. 9, the drill bit 400 includes a mounting end 402 configured to be coupled to an orthopaedic drill, a shank 404 extending from the mounting end 402, and a drill bit end 406. Illustratively, the mounting end 402 of the orthopaedic pilot drill bit 400 includes a Hudson end to facilitate quick intraoperative assembly and use with drills equipped with Hudson-type adaptors. The drill bit end 406 includes a collar 408, drill flutes 410, and a starter bit 412 that extends from the drill flutes 410. Illustratively, the drill flutes 410 have a length 414 of about 5.5 millimeters and a diameter 416 of about 10 millimeters. In use, the collar 408 operates as a depth stop to limit the depth to which the drill bit 400 advances into the distal end of the patient's femur. That is, collar 408 is configured to reference the surrounding cartilage and restrict or limit the advancement of the drill bit 400 further into the patient's bone.

Figure 10:
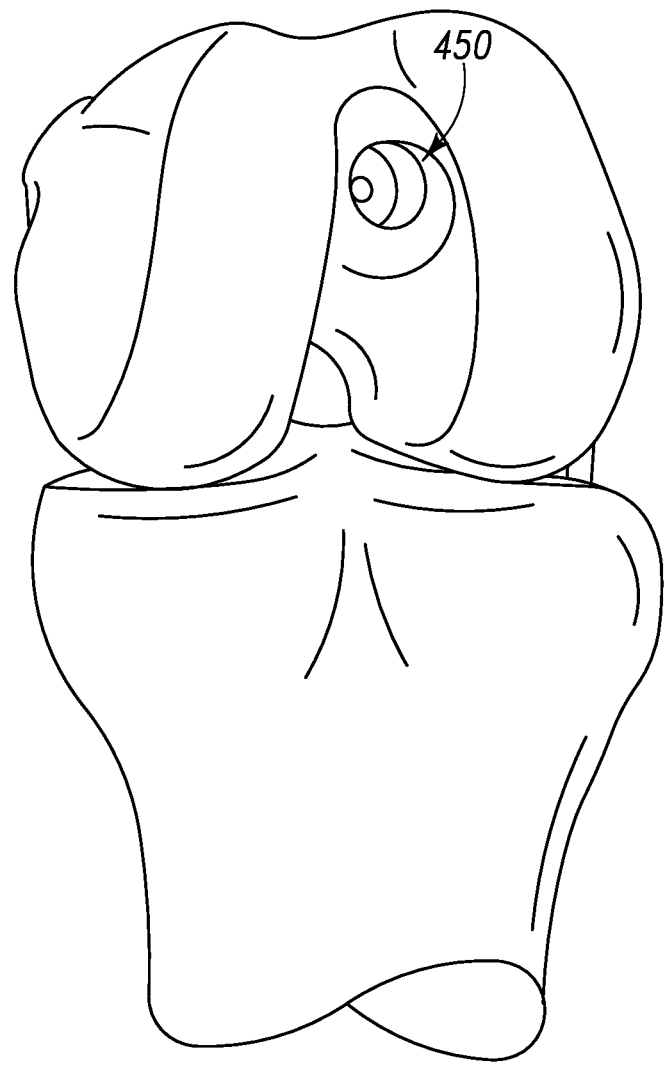
FIG. 10 is a perspective view of the patient's femur having a reference hole defined in the distal end of the femur.

In use, the orthopaedic surgeon positions the starter bit 412 in the pilot hole established in step 16. The pilot hole guides the drill bit 400 as the drill flutes 410 establish a reference hole 450 in the distal end of the patient's femur as illustrated in FIG. 10. The diameter 416 of the drill flutes 410 is sized such that the posterior-most point of the reference hole 450 defined by the flutes 410 corresponds to the distal tip 302 of the trochlear orthopaedic prosthesis 300 (see FIG. 7) when the prosthesis 300 is secured to the patient's femur. That is, the most posterior edge of the reference hole 450 formed by the drill flutes 410 defines the position of the distal tip 302 of the trochlear orthopaedic implant 300. Additionally, because the collar 408 references the surrounding cartilage, the articulating surface of the distal tip of the trochlear orthopaedic implant 300 is substantially parallel or flush with the surrounding cartilage when the implanted in the bone of the patient.

Figure 11:
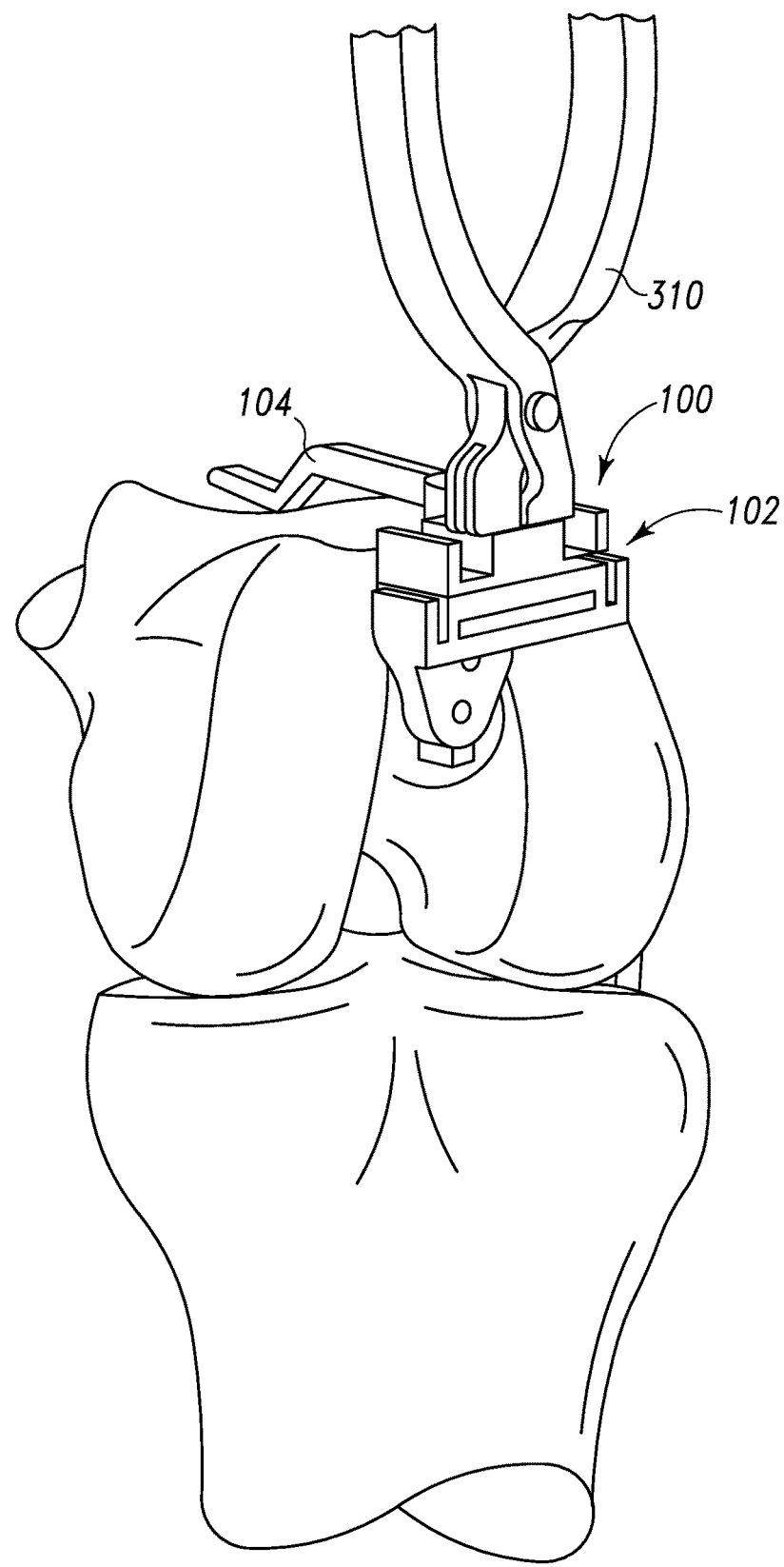
FIG. 11 is a perspective view of the anterior femoral cutting block of FIG. 2 attached to the patient's femur.

Referring back to FIG. 1, after the reference hole 450 has been defined in the distal end of the patient's femur via use of the drill bit 400, the anterior femoral cutting block 100 is coupled to the patient's femur and oriented in step 22. To do so, as shown in FIG. 11, the positioning tool 310 is coupled to the cutting block 100 and used to position the cutting block body 100 on the distal end of the patient's femur. The anterior femoral cutting block 100 is positioned such that the distal boss 154 of the cutting block body 102 is received in the reference hole 450 established in step 20. Once the distal boss 154 is positioned in the reference hole, the anterior femoral cutting block 100 is aligned. To do so, the anterior femoral cutting block 100 is positioned such that the proximal end shaft 204 of the sizing arm 104 is centered on the patient's femur. Additionally, as discussed above, the *Varus/Valgus* alignment of the cutting block body 102 can be evaluated by assessing the quality of fit or conformity of each side of the bone-confronting side 152 of the block body 102.

The axial alignment of the anterior femoral cutting block 100 is also established in step 22. To do so, the top surfaces 128, 130 of the side walls 120, 122 (see FIG. 3) are aligned with the "sky-line" of the associated condyles of the patient's femur. That is, the orthopaedic surgeon may rotate or otherwise move the cutting block body 102 of the block 100 until each of the top surfaces 128, 130 is aligned with the respective femoral condyle. In addition, the reference line 131 of the upper body 104 may be used to guide the axial positioning of the cutting block body 102.

After the anterior femoral cutting block 100 is coupled and aligned to the patient's femur, the cutting block 100 is secured to the distal end of the patient's femur in step 24. The anterior femoral cutting block 100 may be secured via use of a number of bone pins, screws, or similar fasteners. The fasteners may be secured into the femur of the patient through the pin guide holes 156, 158. As discussed above, the superior pin hole 156 is angled to prevent or otherwise limit the anterior femoral cutting block 100 from backing off the bone pins during use (e.g., from vibrations generated by a bone saw).

Figure 12:
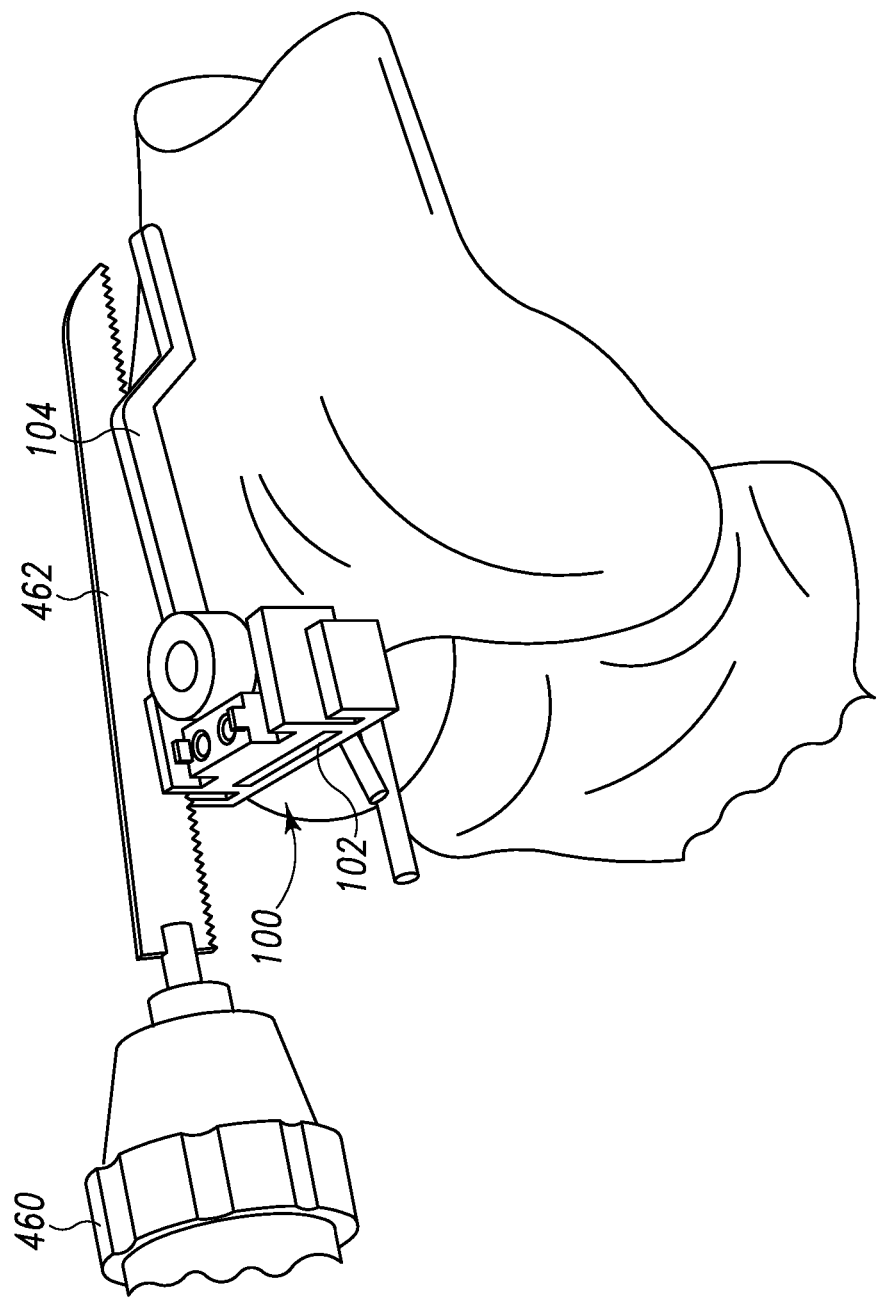
FIG. 12 is a perspective view of a bone saw performing a vertical bone resectioning cut on the patient's femur using the anterior femoral cutting block of FIG. 2.
Figure 13:
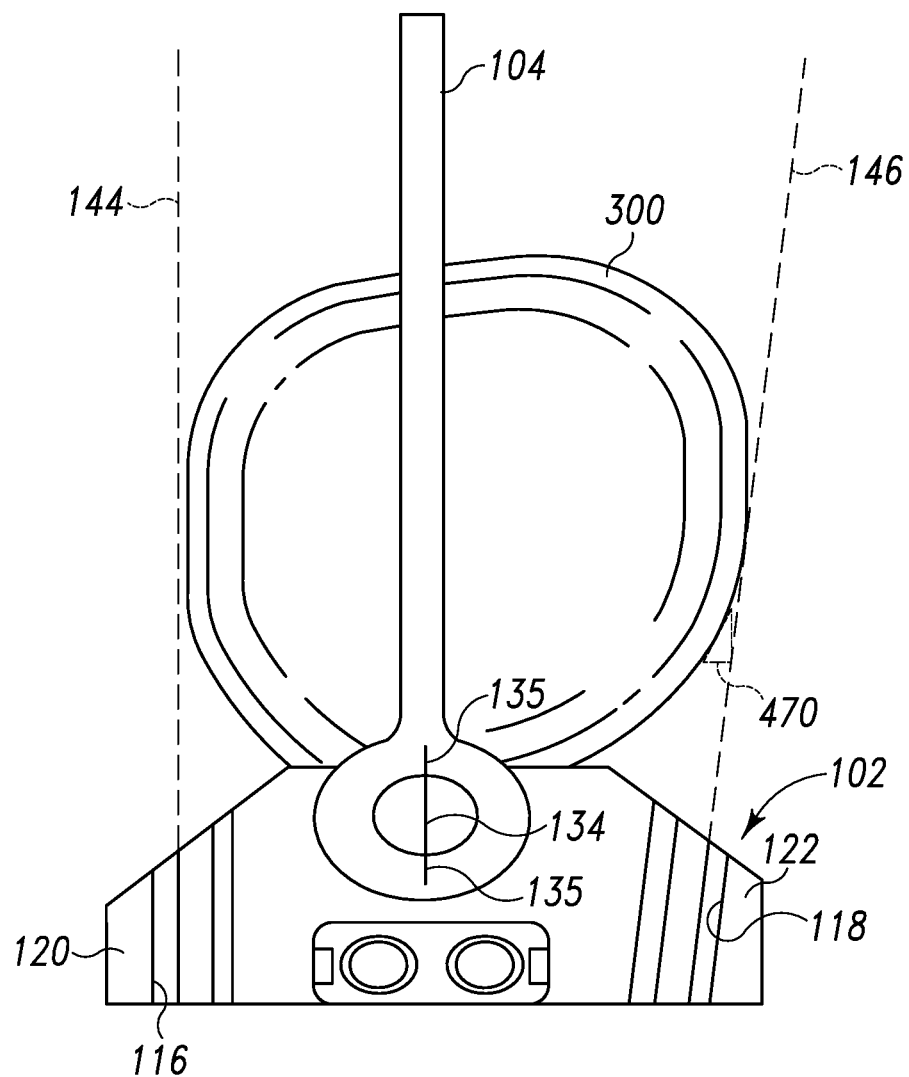
FIG. 13 is a top elevational view of the anterior femoral cutting block of FIG. 2 and a trochlear prosthesis.

Referring back to FIG. 1, after the anterior femoral cutting block 100 has been secured to the patient's femur, the orthopaedic surgeon performs a number of resectioning cuts using the cutting block 100 in steps 26 and 28. In step 26, the orthopaedic surgeon establishes two vertical bone resectioning cuts using a bone saw 460 equipped with a vertical-cutting bone saw blade 462 as shown in FIG. 12. To do so, the vertical cutting guides 116, 118 of the cutting block body 102 are used as guides for the bone saw blade 462. During use, the orthopaedic surgeon may position the vertical bone saw blade 462 against the side walls 120, 122 that define, in part, the vertical cutting guides 116, 118, respectively. As shown in FIG. 13, because the vertical cutting guide 118 is angled relative to the vertical cutting guide 116, the amount of bone removed and not replaced by a portion of the trochlear prosthesis 300 is reduced. The amount of bone removed and not replace by the trochlear prosthesis 300 is simulated or otherwise approximated in FIG. 13 via a triangular indicator 470. It should be appreciated that the triangle 470 (i.e., the amount of bone removed and not replaced by the implant 300) would be substantially larger if the vertical cutting guides 116, 118 were parallel.

Figure 14:
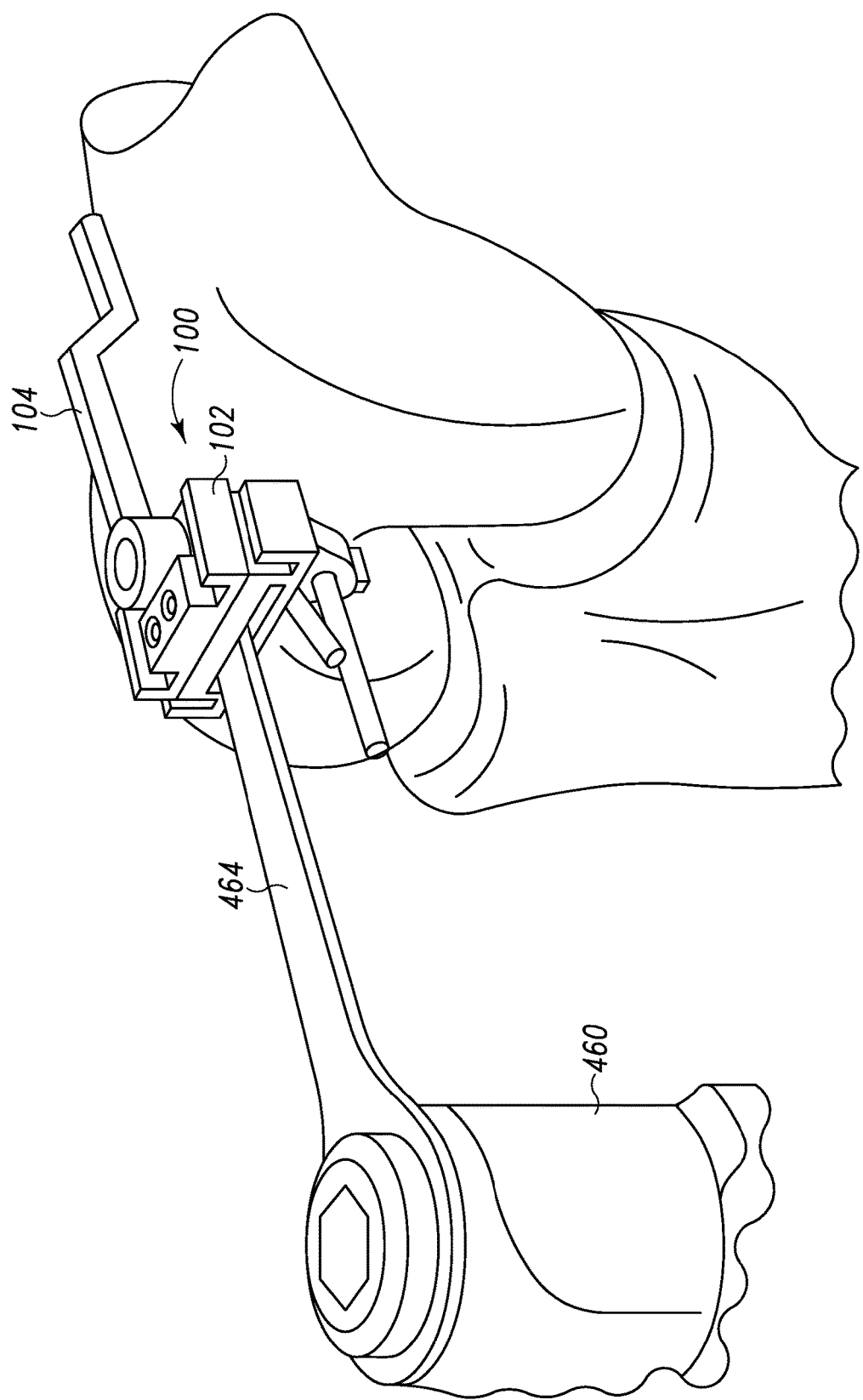
FIG. 14 is a perspective view of a bone saw performing a horizontal bone resectioning cut on the patient's femur using the anterior femoral cutting block of FIG. 2.

After the vertical bone resectioning cuts have been established in step 26, the orthopaedic surgeon uses the anterior femoral cutting block 100 to perform a horizontal resectioning cut using the horizontal cutting guide 114. To do so, as shown in FIG. 14, the orthopaedic surgeon may couple an oscillating saw blade 464 to the bone saw 460 or other oscillating bone saw and position the blade 464 in the horizontal cutting guide 114. During use, the orthopaedic surgeon may position the blade 464 against the bottom wall of the guide 114. It should be appreciated that the horizontal resectioning cut intercepts the pre-established vertical resection cuts to define a portion of the patient's femur that is subsequently removed. By removing the femoral portion, a trochlear cavity sized to receive the trochlear prosthesis 300 is established in the patient's anterior femur. As such, via use of the cutting guides 114, 116, 118, the femur of the patient is prepared for receiving the trochlear orthopaedic prosthesis 300.

Figure 15:
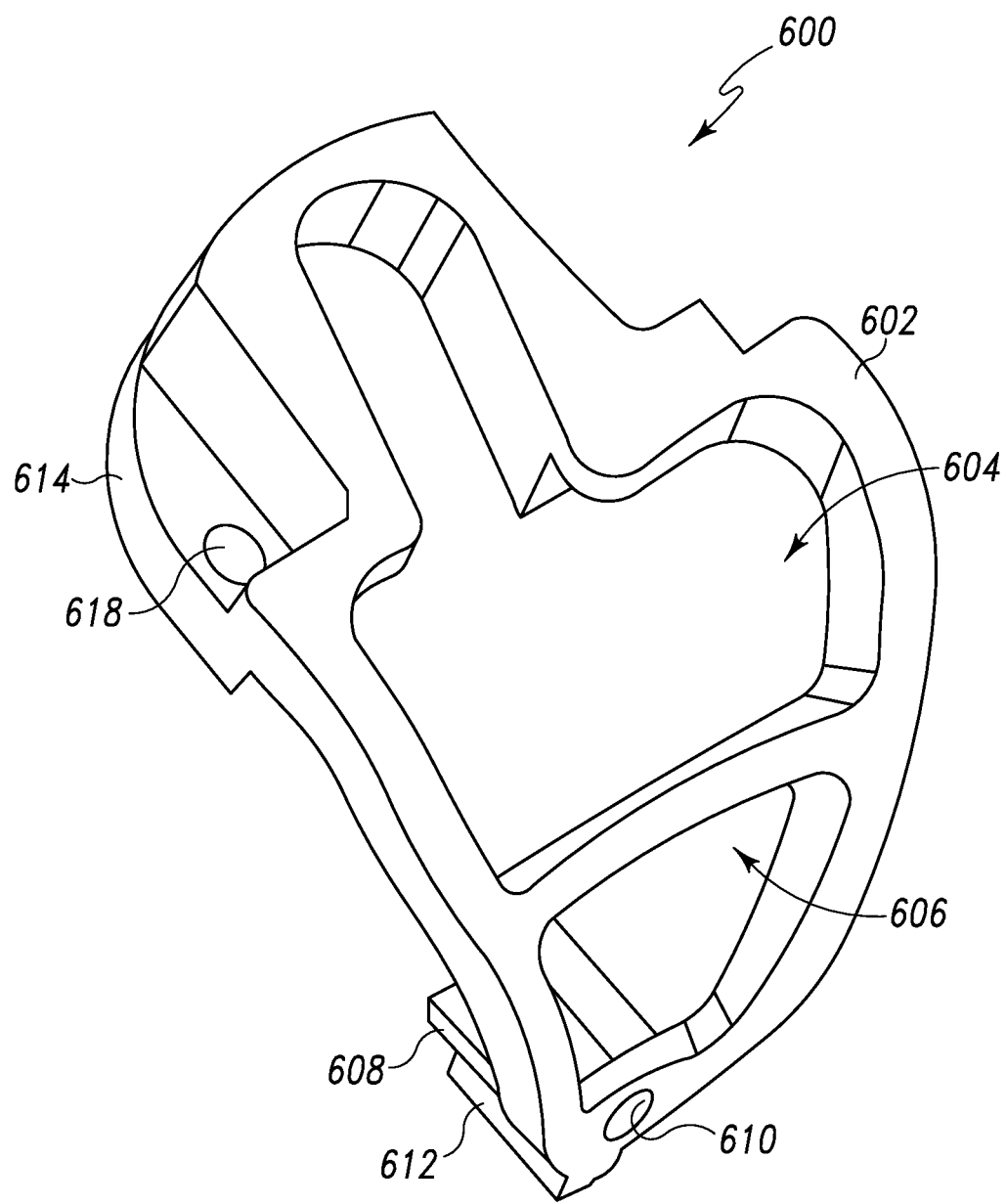
FIG. 15 is a perspective view of a finishing burring guide for use with the method of FIG. 1.
Figure 16:
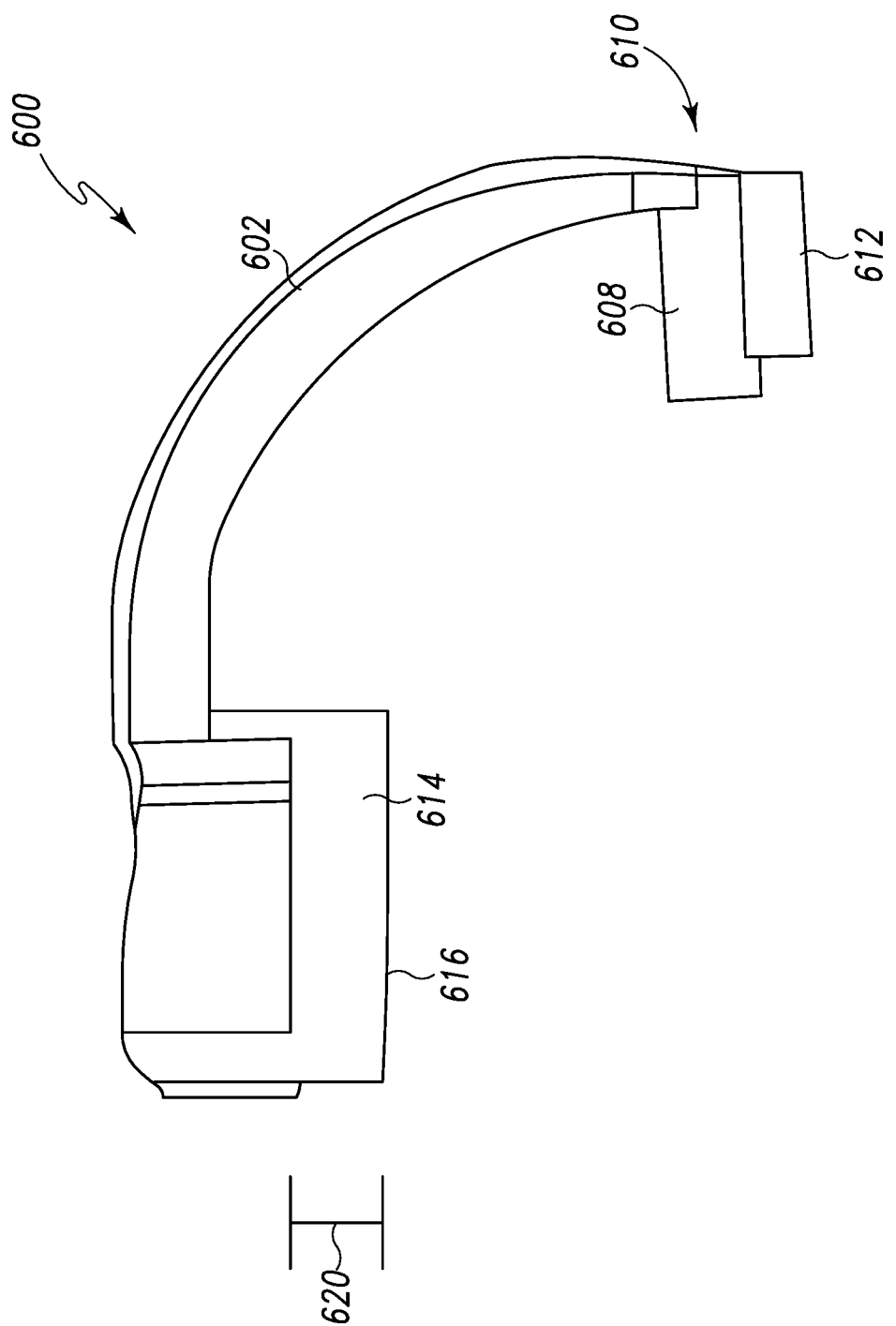
FIG. 16 is a side elevational view of the finishing burring guide of FIG. 15.

After the orthopaedic surgeon has performed all of the bone cuts using the anterior femoral cutting block 100, the cutting block 100 is removed and a finishing burring guide 600 is attached to the patient's femur in step 30. As illustrated in FIGS. 15 and 16, in one embodiment, the burring guide 600 includes a frame 602 defining a superior opening 604 and an inferior opening 606. The guide 600 includes a distal boss 608, which is configured to be received in the reference hole 450 defined in the patient's bone in step 20. Additionally, the guide 600 includes a pin guide hole 610 defined through the distal boss 608, which is positioned to receive the bone pin used to secure the cutting block body 102 to the patient's femur via the guide pin hole 158. The guide 600 also includes a distal tab 612 that extends downwardly from the frame 602. Similar to the tab 160 of the cutting block body 102, the tab 612 is configured to reference the surrounding cartilage of the patient's femur.

As shown in FIG. 16, the burring guide 600 also includes a base 614 coupled to a proximal end of the frame 602. The base 614 is configured to be received in the proximal portion of the trochlear cavity formed in steps 26, 28 of the method 10. That is, the base 614 includes a bottom surface 616 configured to abut or confront the resectioned bone of the patient's femur. The base 614 includes a number of mounting holes 618 for further securing the guide 600 to the patient's femur.

Figure 17:
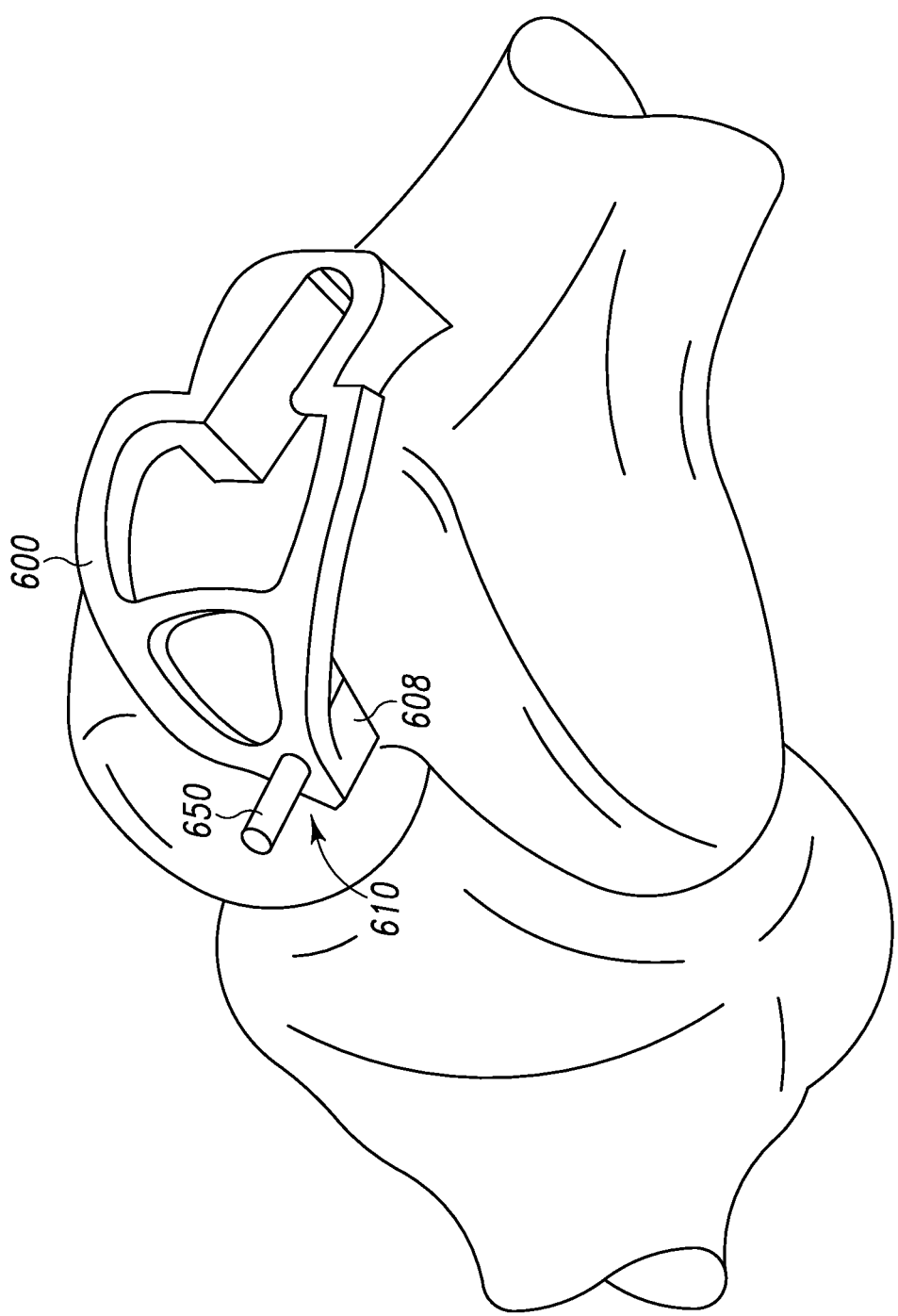
FIG. 17 is a perspective view of the finishing burring guide of FIG. 15 being coupled to the distal end of the patient's femur.

As illustrated in FIG. 17, the burring guide 600 is coupled to the distal end of the patient's femur such that the distal boss 608 is received in the reference hole 450. To do so, the guide pin 650 that was used to secure the cutting block body 102 (via the guide pin hole 158 of the distal boss 154) is received in the guide pin hole 610 defined in the distal boss 608. The burring guide 600 is slid forward along the guide pin 650 and positioned such that the distal boss 608 is received in the reference hole 450. Additionally, the base 614 is received in the trochlear cavity defined in steps 26, 28 and contacts or abuts the resection bone of the patient's femur. The burring guide 600 may be further secured to the patient's femur via use of a number of Steinman pins, bone screws, or other fasteners positioned in the mounting holes 618. The base 614 of the guide 600 has a thickness 620 (see FIG. 16) that is substantially equal to the thickness of the anterior portion of the trochlear orthopaedic prosthesis 300. As such, the upper ledges of the base 614 may be used by the surgeon to confirm the anterior resection depth relative to the surrounding bone.

Figure 18:
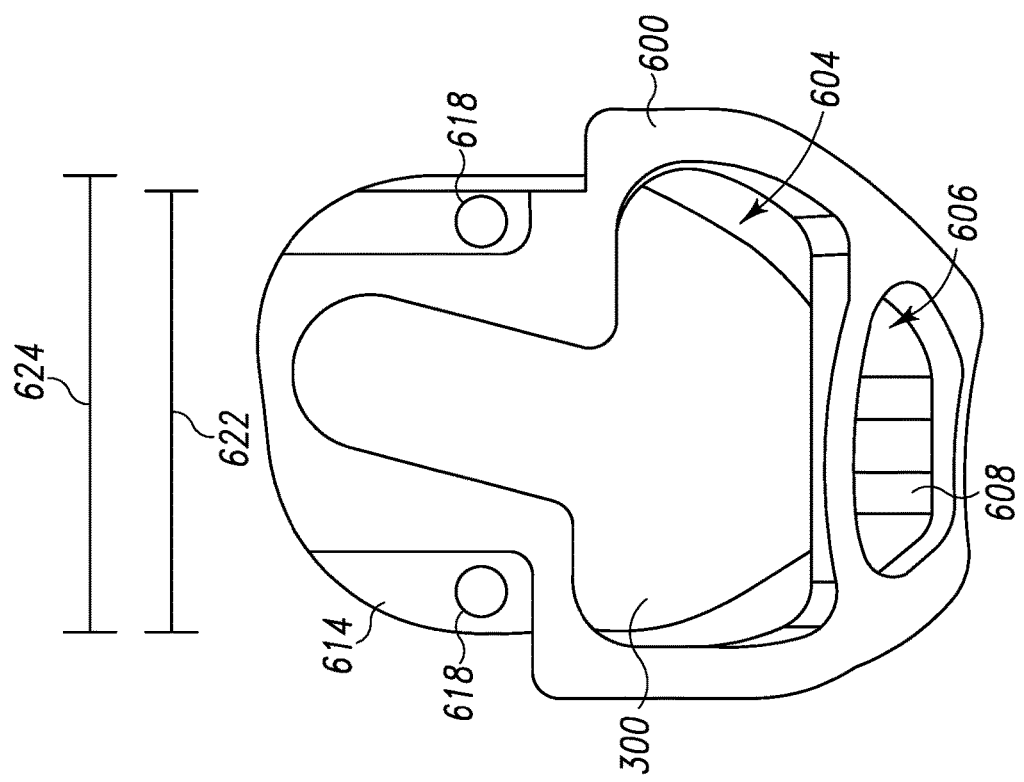
FIG. 18 is a top elevational view of the finishing burring guide of FIG. 15 and the trochlear prosthesis.

As shown in FIG. 18, the base 614 has a width 622 that is less than the width of the selected trochlear orthopaedic implant 300. The width 622 is so sized due to the angled vertical resection that is established using the cutting block 100 in steps 26, 28. That is, because of the angled cut established using the vertical cutting guide 118, the proximal end of the burring guide 600 is narrower to allow the proximal end of the guide 600 to slide within the narrowest width of the trochlear cavity defined in the patient's femur in steps 26, 28.

Figure 19:
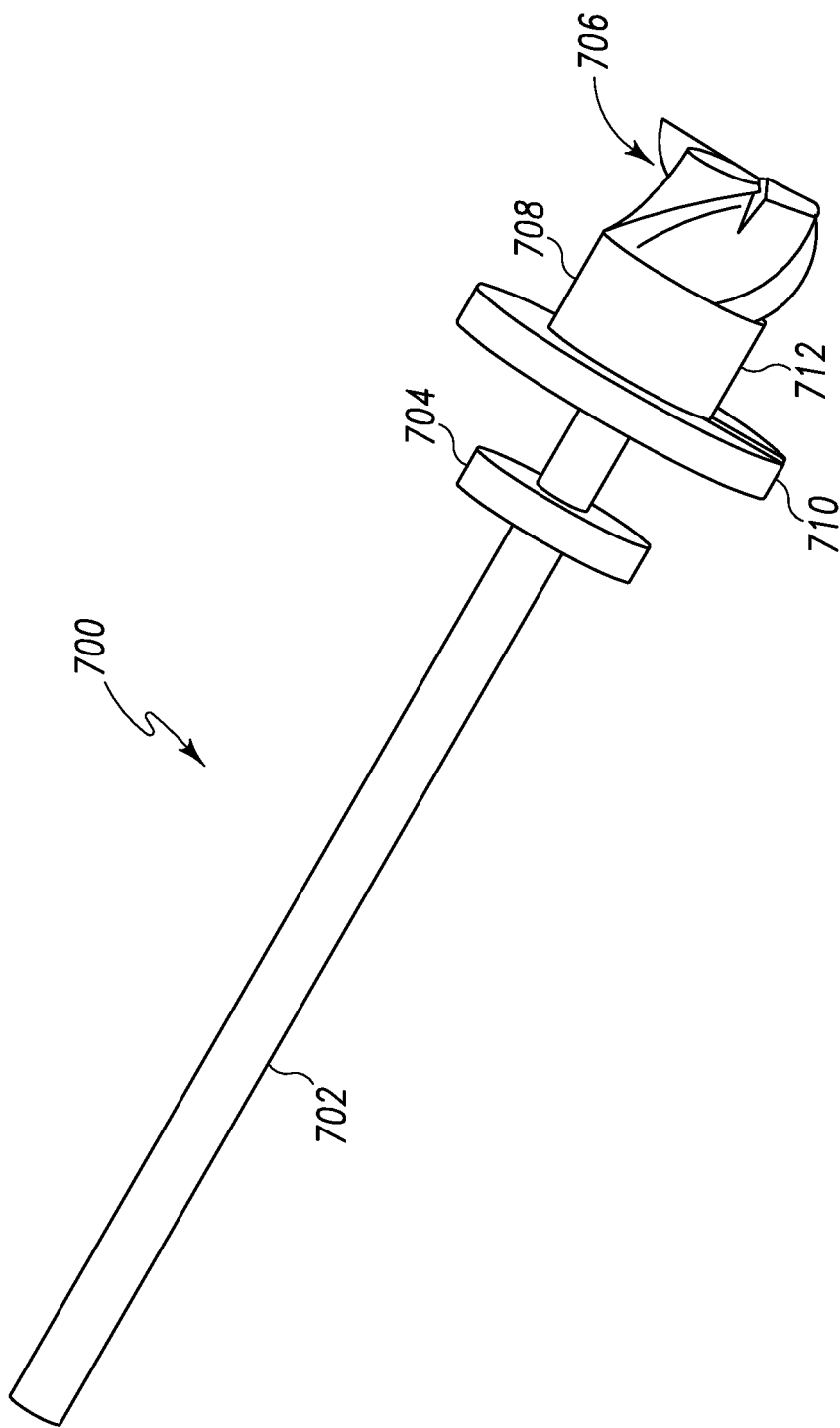
FIG. 19 is a perspective view of a burring bit for use with the finishing burring guide of FIG. 15.

Referring back to FIG. 1, after the finishing guide 600 is attached to the patient's femur as discussed above, the trochlear cavity formed in the patient's femur is further defined and/or enlarged via a burring process in step 32. To do so, the frame 602 of the guide 600 is used as a burring guide for a burring bit. As illustrated in FIG. 19, in one embodiment, a burring bit 700 that may be used with the finishing guide 600 includes an elongated shaft 702, a collar 704, and a burring end 706. The burr bit 700 also includes a washer 708 positioned around the shaft 702 between the collar 704 and the burring end 706. The washer 708 includes a circular collar 710 and a cylindrical neck 712 extending downwardly from the collar 710. As discussed in more detail below, the collar 710 of the washer 708 is used as a movable guide or rest against the burring guide 600. Illustratively, the washer 708 is a PEEK™ washer.

Figure 20:
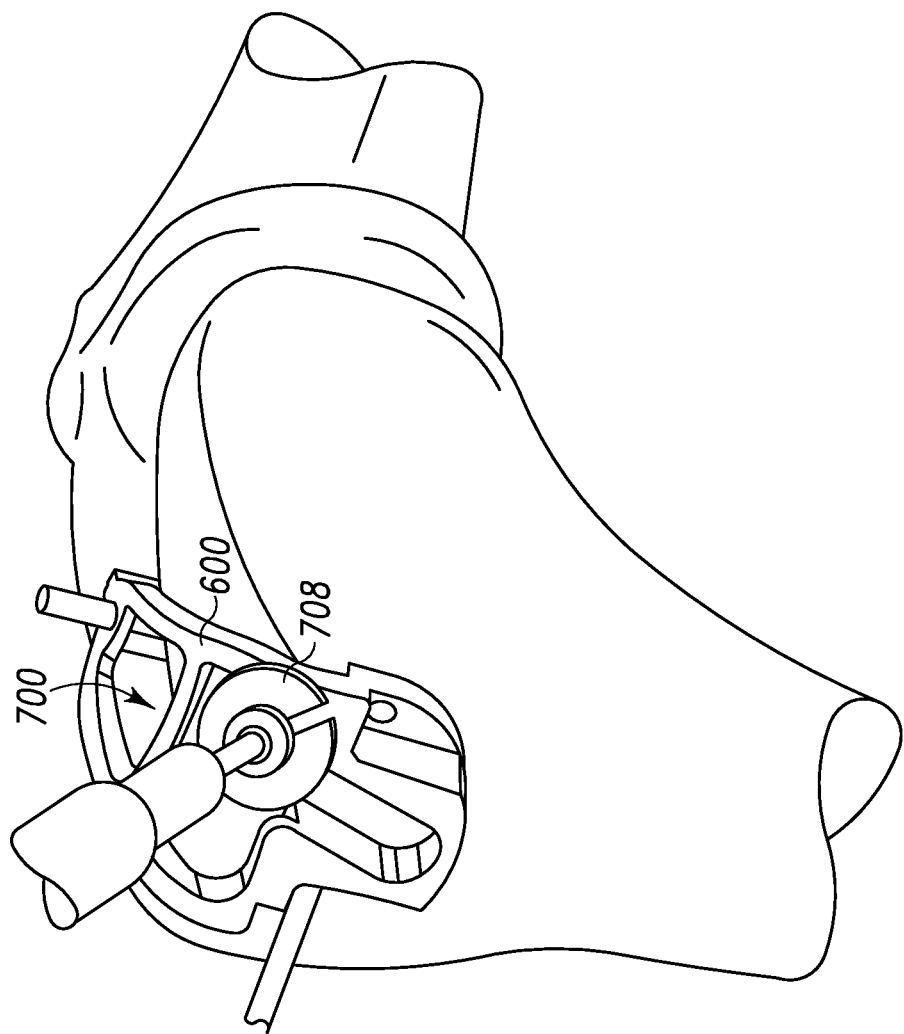
FIG. 20 is a perspective view of the burring bit of FIG. 19 used with the finishing burring guide of FIG. 15 to remove a portion of the patient's anterior and distal femur.

In use, as illustrated in FIG. 20, the burring bit 700 is inserted in one of the openings 604, 606 of the burring guide 600. The collar 704 of the burring bit 700 controls the depth to which the burring bit 700 advances into the patient's bone. The burring bit 700 may be used to resect additional bone by moving the burring bit 700 along the frame 602. When doing so, the washer 708 contacts the frame 602. The interfacing of the washer 708 to the frame 602 may reduce heat generated during the cutting operation. The washer 708 may or may not rotate with the elongated shaft 702 of the burring bit 700. The burr bit 700 may be moved along the frame 602 while keeping the washer 708 in contact with the frame 602.

Referring back to FIG. 1, after the trochlear cavity is initially burred in step 32 using the burring guide 600 and the burring bit 700, a trochlear trial is positioned in the trochlea cavity and the "fit" of the trochlear trial is determined in step 34. In one particular embodiment, the trochlea trial is formed from a substantially transparent material, such as a plastic material, to allow the orthopaedic surgeon to visually inspect the "fit" of the trochlear trial. If required, the trochlear cavity may be further detailed using the burring bit 700 in step 36 and the trochlear trial may be repositioned in the trochlear cavity. The blocks 34 and 36 may be repeatedly performed to ensure a proper fit of the trochlear trial.

Figure 21:
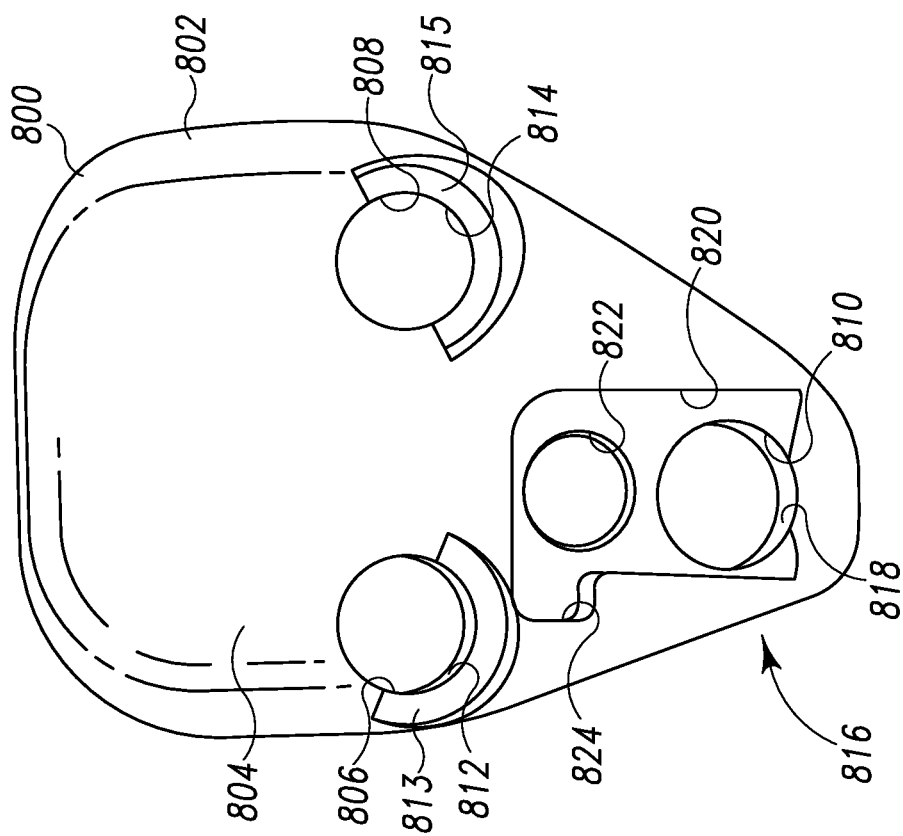
FIG. 21 is a top plan view of a pegless trochlear prosthetic trial for use in the method of FIG. 1.

Once satisfied of the trochlear trial fit, peg holes for receiving the pegs of the trochlear orthopaedic prosthesis 300 are formed in the patient's femur. To do so, in step 38, the orthopaedic surgeon positions a pegless trochlear prosthetic trial 800 in the trochlear cavity formed in the patient's femur in step 38. As shown in FIG. 21, in one embodiment, the pegless trochlear prosthetic trial 800 includes a body 802 shaped substantially similar to the trochlear prosthesis 300. The body 802 includes an outer or top surface 804 and three drill guide holes 806, 808, 810. The drill guide holes 806, 808, 810 are positioned on the body 802 of the trial 800 at locations corresponding to the pegs of the trochlear orthopaedic prosthesis 300. As discussed below, the drill guide holes 806, 808, 810 provide a guide for establishing peg holes in the patient's femur.

In the illustrative embodiment, the guide holes 806, 808 are located superiorly relative to the guide hole 810 and are substantially parallel to each other in the medial-lateral direction. Each of the guide holes 806, 808 includes an opening 812, 814, respectively, recessed or partially recessed relative to the outer surface 804 of the trial 800. A recess flange 813, 815 is defined around or partially around each opening 812, 814. The trochlear prosthetic trail 800 also includes a mounting platform 816 positioned inferiorly relative to the guide holes 806, 808. The mounting platform 816 is recessed relative to the upper surface 804 of the trial 800. The mounting platform 816 is shaped to receive a base of a trochlear drill guide 900 as discussed in more detail below.

In the illustrative embodiment of FIG. 21, the mounting platform 816 includes a recessed area 820 having a generally wedge or triangular shape. However, the recessed area 820 may have other shapes corresponding to the base of the drill guide 900 in other embodiments. An opening 818 of the guide hole 810 is located in the recessed area 820 of the mount platform 816. Additionally, the trochlear prosthetic trail 800 includes a mounting aperture 822 defined in the recessed area 820 of the mount platform 816. The mounting aperture 822 provides a location to which the drill guide 900 may be secured to the trial 800 as discussed in more detail below. As such, in some embodiment, the mounting aperture 822 may be threaded and configured to receive a bolt or similar fastener to secure the drill guide 800 to the trochlear prosthetic trial 800. In the illustrative embodiment, the mount platform 816 is keyed. That is, the mount platform 816 includes key recess area 824, which is in communication with the recessed area 820. Illustratively, the key recess area 824 extends from a side of the recessed area 820, but may be positioned in other locations in other embodiments. The key recess area 824 ensures that the drill guide 900 is secured to the trial 800 in the proper orientation as discussed in more detail below.

Figure 22:
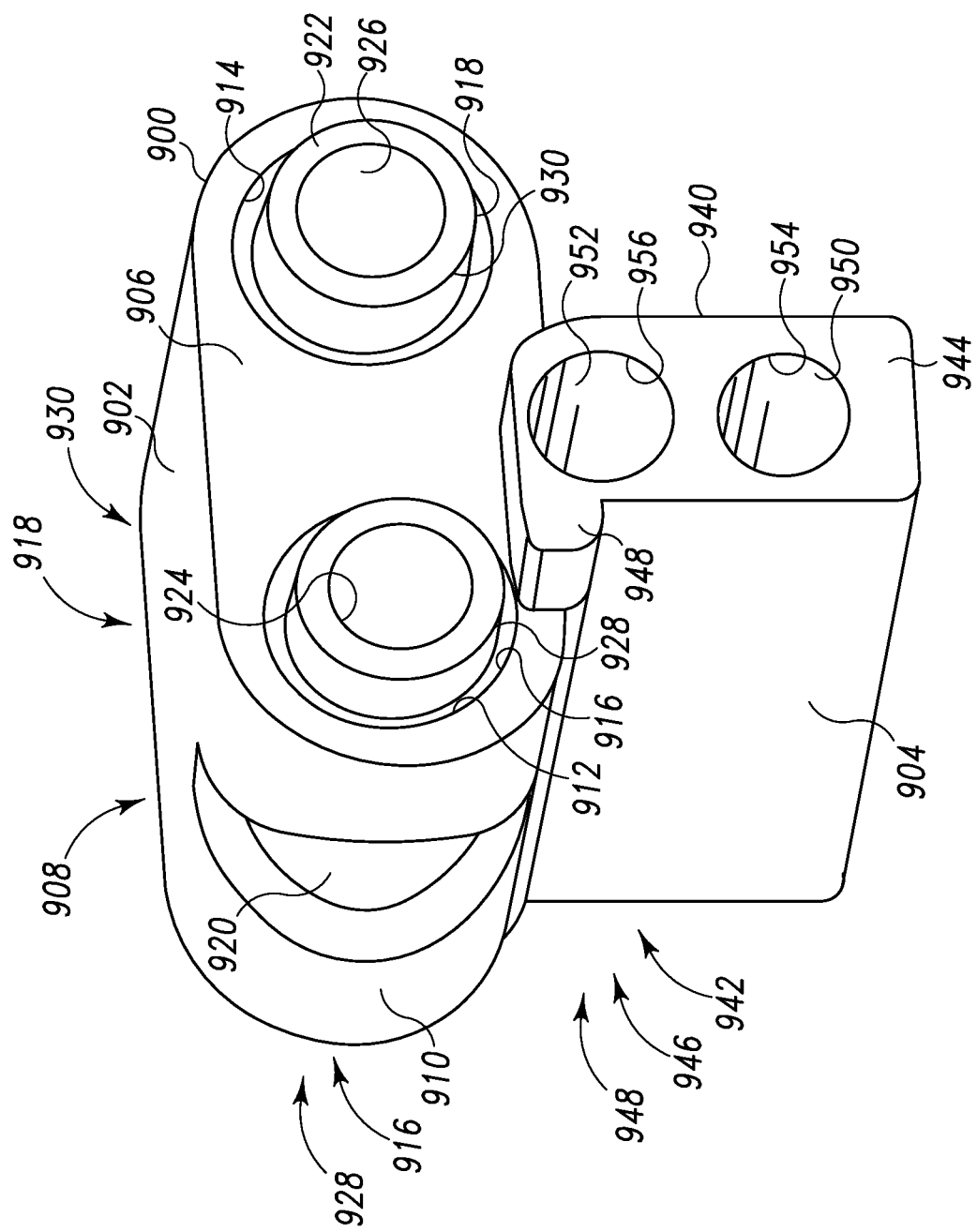
FIG. 22 is a perspective view of a trochlear drill guide for use with the method of FIG. 1.
Figure 23:
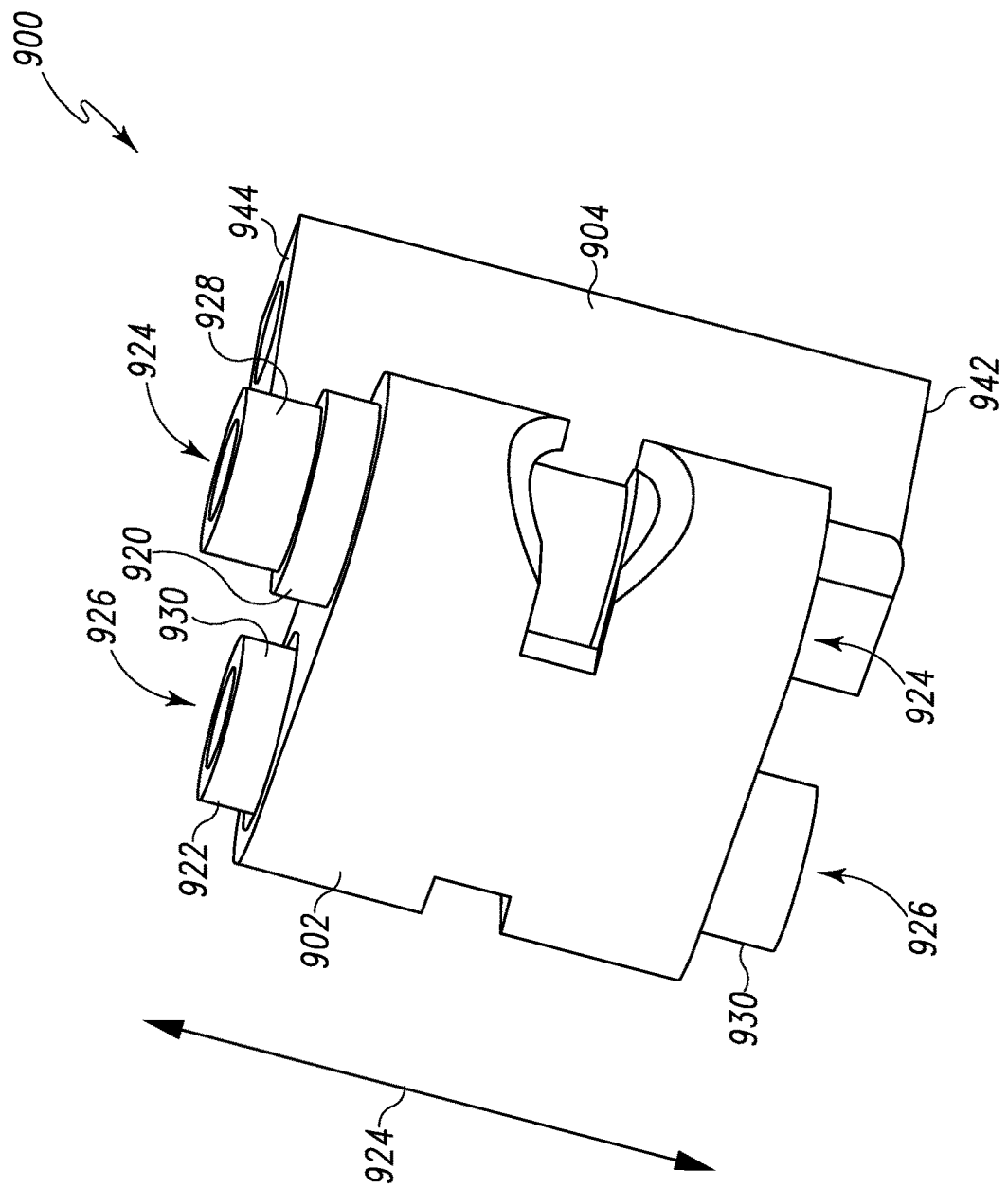
FIG. 23 is another perspective view of the trochlear drill guide of FIG. 22.
Figure 24:
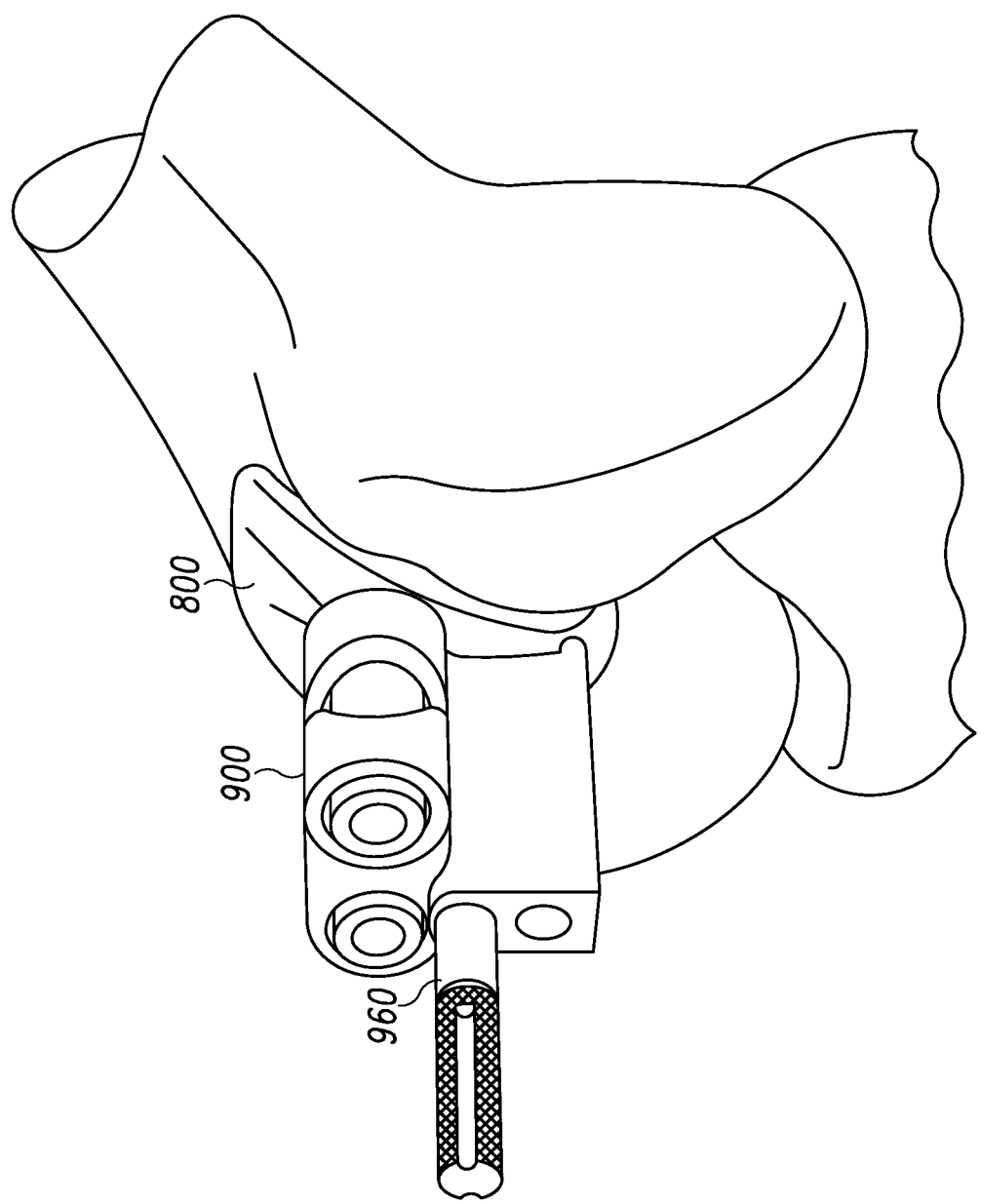
FIG. 24 is a perspective view of the trochlear drill guide of FIG. 22 coupled to the patient's femur.

After the trochlear prosthetic trial 800 has been positioned in the trochlear cavity formed in the patient's femur, the trochlear drill guide 900 is attached or secured to the trochlear trial 800 in step 40. As illustrated in FIGS. 22-24, in one embodiment, the trochlear drill guide 900 includes a body 902 and a mount 904 extending from the body 902. Illustratively, the body 902 has a substantially oval shape, but may have other shapes in other embodiments. The illustrative body 902 includes substantially planar upper surfaces 906, 908 and a curved sidewall 910 extending between the upper surfaces 906, 908. Two passageways 912, 914 are defined through the body 902. Each of the passageways 912, 914 include an opening 916, 918, respectively, defined in each of the upper surfaces 906, 908.

The illustrative drill guide 900 also includes two drill guide bushings 920, 922 positioned in the passageways 912, 914, respectively. However, it should be appreciated that, in other embodiments, the drill guide 900 may include a single or multiple bushings positioned in corresponding passageways. The bushings 920, 922 are separately movable within the passageways in a direction 924 (see FIG. 23) toward and away from the upper surfaces 906, 08. In the illustrative embodiment, the drill guide bushings 920, 922 are retained in the passageways 912, 914, respectively. That is, the drill guide bushings 920, 922 are movable in the passageways 912, 914, but cannot be removed therefrom. However, in other embodiments, the drill guide bushings 920, 922 may be removable from the passageways 912, 914. Each of the drill guide bushings 920, 922 includes a drill guide passageway 924, 926 defined thorough and a mounting collar 928, 930 at both ends of the bushing 920, 922. In use, when the drill guide 900 is coupled to the trochlear trial 800, the mounting collars 924, 926 independently contact the recessed flanges 813, 815 of the trial 800 and the drill guide passageways 924, 926 align with the drill guide holes 806, 808 of the trail 800.

As discussed above, the bushings 920, 922 are independently positionable within their respective passageway 912, 914. The position of the bushings 920, 922 and the thickness of the recessed flanges 813, 815 of the trochlear trial 800 define the depth the peg holes are drilled into the patient's femur (i.e., the orthopaedic drill stops advancing when it contacts the bushing 920, 922). As such, the trochlear drill guide 900 is usable with trochlear trials of various sizes. That is, because the bushings 920, 922 are independently adjustable, the drill guide 900 may be used with trials 800 having various dimensions such as thickness and overall size.

As shown in FIG. 22, the mount 904 includes a mount base 940, 942 on each upper side 944, 946 of the mount 904. The mount bases 940, 942 are shaped and sized to be received in the recessed mount platform 816 of the trial 800. In the illustrative embodiment, each of the mount bases 940, 942 are keyed and include a key protrusion 948, which is configured to be received in the key recess area 824 of the recessed mount platform 816 which the drill guide 900 is coupled to the trial 800. The key protrusion 948 and the key recess area 824 cooperate to limit the orientation of the trochlear drill guide 900. That is, the trochlear drill guide 900 is configured to couple to a right knee trochlear trial in one configuration and couple to a left knee trochlear trial in a second configuration. To do so, the surgeon simply flips the drill guide 900 over such that the correct mount base 940, 942 is received in the recess mount platform 816. In this way, the drill guide 900 is usable with trochlear prosthetic trials 800 designed for either right or left knees (as well as different sizes of right and left knee trials 800 as discussed above)

The trochlear drill guide 900 also includes a drill guide passageway 950 and a fastener passageway 952 defined through the mount 904. Each of the passageways 950, 952 include a respective opening 954, 956 defined on each mount base 940, 942. When the trochlear drill guide 900 is attached to the trochlear prosthetic trial 800, the drill guide passageway 950 aligns with the guide hole 810 of the trial 800 and the fastener passageway 952 aligns with the mounting aperture 822 of the trial 800. As shown in FIG. 24, the trochlear drill guide 900 may be secured to the trochlear prosthetic trial 800 by inserting a lock rod, bolt, or other fastener 960 through the fastener passageway 952 and threading the fastener 960 into the mounting aperture 822 of the trial 800. When so secured, the drill guide passageways 924, 926, 950 align with the drill guide holes 806, 808, 810 of the trial 800 as discussed above.

Figure 25:
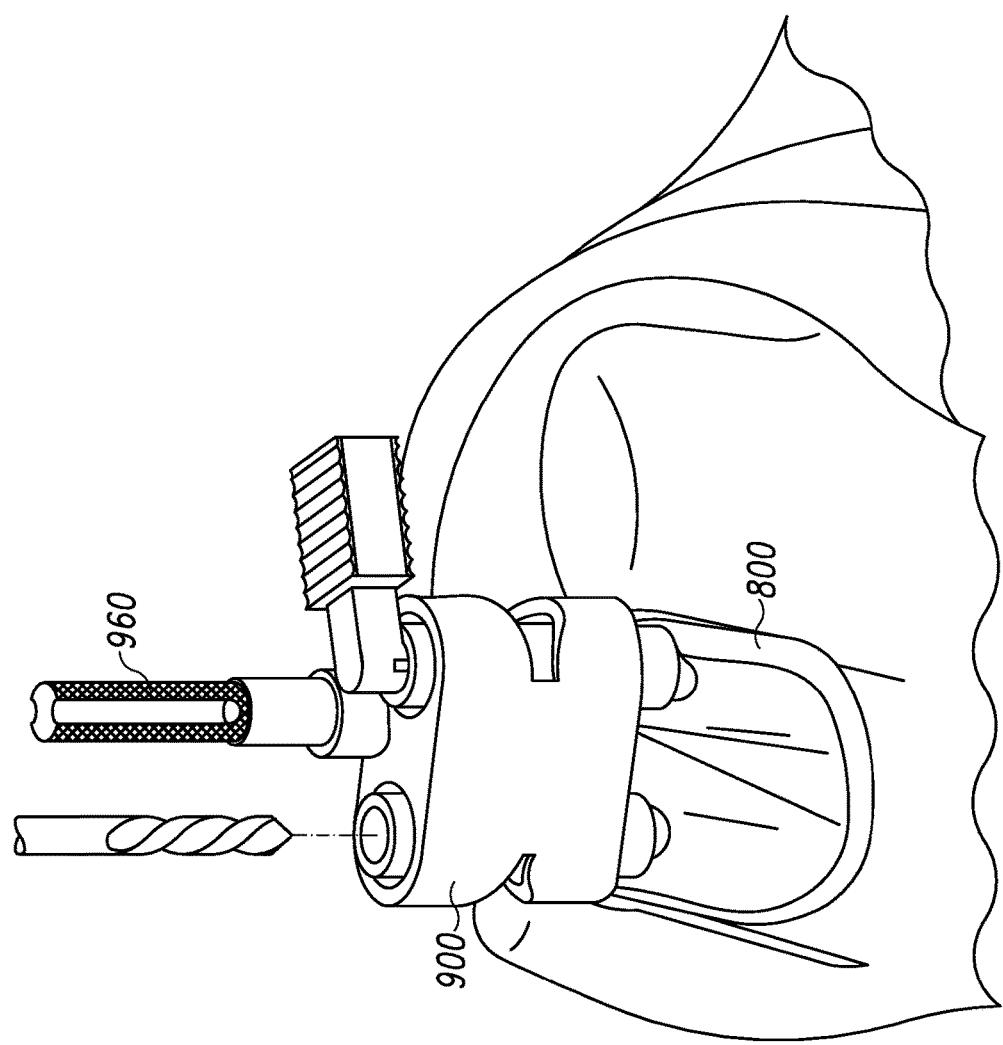
FIG. 25 is a perspective view of the trochlear drill guide of FIG. 22 secured to the patient's femur during an orthopaedic drilling procedure.

After the trochlear drill guide 900 has been secured to the trochlear prosthetic trial 800, the orthopaedic surgeon may drill the peg holes into the patient's surgically-prepared femur using the drill guide 900 and the trial 800 in step 42. To do so, as illustrated in FIG. 25, a bone drill bit is inserted into each of the drill guide passageways 924, 926, 950. After a peg hole has been established in the patient's femur, the orthopaedic surgeon may insert a locking or stabilizing rod into the relevant drill guide passageway 924, 926, 950 to keep the guide 900 and trial 800 aligned with previously drilled peg holes while the remaining peg holes are established.

After the orthopaedic surgeon has formed the peg holes in the patient's femur, the orthopaedic surgeon may subsequently implant the trochlear prosthesis 300 into the patient's surgically-prepared femur. As discussed above, because the anterior femoral cutting block 100 was used to establish the trochlear cavity, the trochlear prosthesis 300 is inlaid into the patient's femur rather than resting on an outer surface of the femur.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the methods, devices, and assemblies described herein. It will be noted that alternative embodiments of the methods, devices, and assemblies of the present disclosure may not include all of the features described yet still benefit from at least some of the advantages of such features. Those of ordinary skill in the art may readily devise their own implementations of the methods, devices, and assemblies that incorporate one or more of the features of the present invention and fall within the spirit and scope of the present disclosure as defined by the appended claims.

The invention claimed is:

1. An orthopaedic surgical instrument comprising:
a burring guide configured to guide a surgical burr to resect bone from a patient's femur, the burring guide comprising:
a frame having a curved bone-facing side and defining a first opening and a second opening separate from the first opening, both the first opening and the second opening being shaped to guide the surgical burr to resect bone from the patient's femur;
a distal boss extending from the bone-facing side of an inferior end of the frame, the distal boss including a passageway defined therein; and
a base extending downwardly from a superior end of the frame, the base being sized to be received in a surgically-prepared trochlear cavity of a patient's femur, the base including a first and second mounting hole defined therethrough.

2. The orthopaedic burring guide of claim 1, further comprising a tab extending downwardly from the distal boss, the tab having a length less than the distal boss and being positioned to contact distal cartilage of the patient's femur when the orthopaedic burring guide is coupled to the patient's femur.

3. The orthopaedic burring guide of claim 1, wherein the distal boss is configured to be received in a surgically-prepared reference hole of the patient's femur.

4. The orthopaedic burring guide of claim 3, wherein the passageway defined in the distal boss is sized to receive a guide pin, and wherein the distal boss is configured to slide along the guide pin into the reference hole of the patient's femur.

5. The orthopaedic burring guide of claim 1, wherein the base includes a distal end and a proximal end positioned opposite the distal end, and the distal end has a first width and the proximal end has a second width less than the first width.

* * * * *